United States Patent
McMillan et al.

(10) Patent No.: US 9,326,823 B2
(45) Date of Patent: May 3, 2016

(54) REAL-TIME TRACKING AND NAVIGATION SYSTEM AND METHOD FOR MINIMALLY INVASIVE SURGICAL PROCEDURES

(71) Applicants: UNIVERSITY OF MARYLAND, BALTIMORE, Baltimore, MD (US); University of Maryland, College Park, College Park, MD (US)

(72) Inventors: Alan B. McMillan, Madison, WI (US); Rao Gullapalli, Ellicott City, MD (US); Howard M. Richard, III, Clarksville, MD (US); Steven Roys, Finksburg, MD (US); Jaydev P. Desai, Bethesda, MD (US)

(73) Assignees: University of Maryland, College Park, College Park, MD (US); University of Maryland, Baltimore, Baltimore, MD (US)

( * ) Notice: Subject to any disclaimer, the term of this patent is extended or adjusted under 35 U.S.C. 154(b) by 293 days.

(21) Appl. No.: 13/875,849

(22) Filed: May 2, 2013

(65) Prior Publication Data
US 2013/0296737 A1    Nov. 7, 2013

Related U.S. Application Data

(63) Continuation-in-part of application No. 13/763,284, filed on Feb. 8, 2013.

(60) Provisional application No. 61/641,482, filed on May 2, 2012.

(51) Int. Cl.
*A61B 5/05*    (2006.01)
*A61B 19/00*   (2006.01)
(Continued)

(52) U.S. Cl.
CPC ............ *A61B 19/2203* (2013.01); *A61B 10/02* (2013.01); *A61B 17/00234* (2013.01);
(Continued)

(58) Field of Classification Search
CPC ............ A61B 10/02; A61B 17/00234; A61B 18/042; A61B 18/1492; A61B 18/201; A61B 19/2203; A61B 19/5244; A61B 2018/00446; A61B 2017/00477; A61B 2018/00577; A61B 5/055; A61B 2019/5251; A61B 8/0841; A61B 2019/2246; A61N 7/022
USPC .................................. 600/407–460; 606/130
See application file for complete search history.

(56) References Cited

U.S. PATENT DOCUMENTS 8,620,473 B2 * 12/2013 Diolaiti .............. A61B 19/2203
                                                              600/407
9,138,129 B2 *  9/2015 Diolaiti .............. A61B 1/00087
(Continued)

*Primary Examiner* — Sanjay Cattungal
(74) *Attorney, Agent, or Firm* — Rosenberg, Klein & Lee

(57) ABSTRACT

Telemetrical control of a robotic interventional device for minimally invasive surgical procedure is based on an operative interaction between a tracking sub-system, MRI sub-system, navigation sub-system and the robotic interventional device. The tracking sensor sub-system is integrated with the interventional device to produce tracking information corresponding to the robotic interventional device location in the operative site. The navigation sub-system integrates the tracking information with the real-time images of the operative site produced by the MRI sub-system, and displays the integrated information to a user, to enable the telemetrical control of the interventional device for performing an intended procedure (biopsy, tissue resection, etc.). The navigation sub-system, based on the integrated real-time tracking information and real-time images, calculates and dynamically updates coordinates of subsequent imaging slices.

19 Claims, 12 Drawing Sheets

(51) Int. Cl.
  *A61B 10/02* (2006.01)
  *A61B 17/00* (2006.01)
  *A61B 18/20* (2006.01)
  *A61B 6/03* (2006.01)
  *A61B 8/08* (2006.01)
  *A61N 7/02* (2006.01)
  *A61B 5/055* (2006.01)
  *A61B 18/04* (2006.01)
  *A61B 18/14* (2006.01)
  *A61B 18/00* (2006.01)

(52) U.S. Cl.
  CPC ........... *A61B18/201* (2013.01); *A61B 19/5244* (2013.01); *A61B 5/055* (2013.01); *A61B 6/032* (2013.01); *A61B 8/0841* (2013.01); *A61B 18/042* (2013.01); *A61B 18/1492* (2013.01); *A61B 2017/00477* (2013.01); *A61B 2018/00446* (2013.01); *A61B 2018/00577* (2013.01); *A61B 2019/2238* (2013.01); *A61B 2019/2246* (2013.01); *A61B 2019/5251* (2013.01); *A61N 7/022* (2013.01)

(56) References Cited

U.S. PATENT DOCUMENTS

| | | | | |
|---|---|---|---|---|
| 2007/0103437 | A1* | 5/2007 | Rosenberg | A61B 19/22 345/161 |
| 2009/0326318 | A1* | 12/2009 | Tognaccini | A61B 1/00183 600/104 |
| 2012/0059378 | A1* | 3/2012 | Farrell | A61B 17/1626 606/80 |
| 2013/0278631 | A1* | 10/2013 | Border | G02B 27/017 345/633 |
| 2013/0296737 | A1* | 11/2013 | McMillan | A61B 19/2203 600/562 |

* cited by examiner

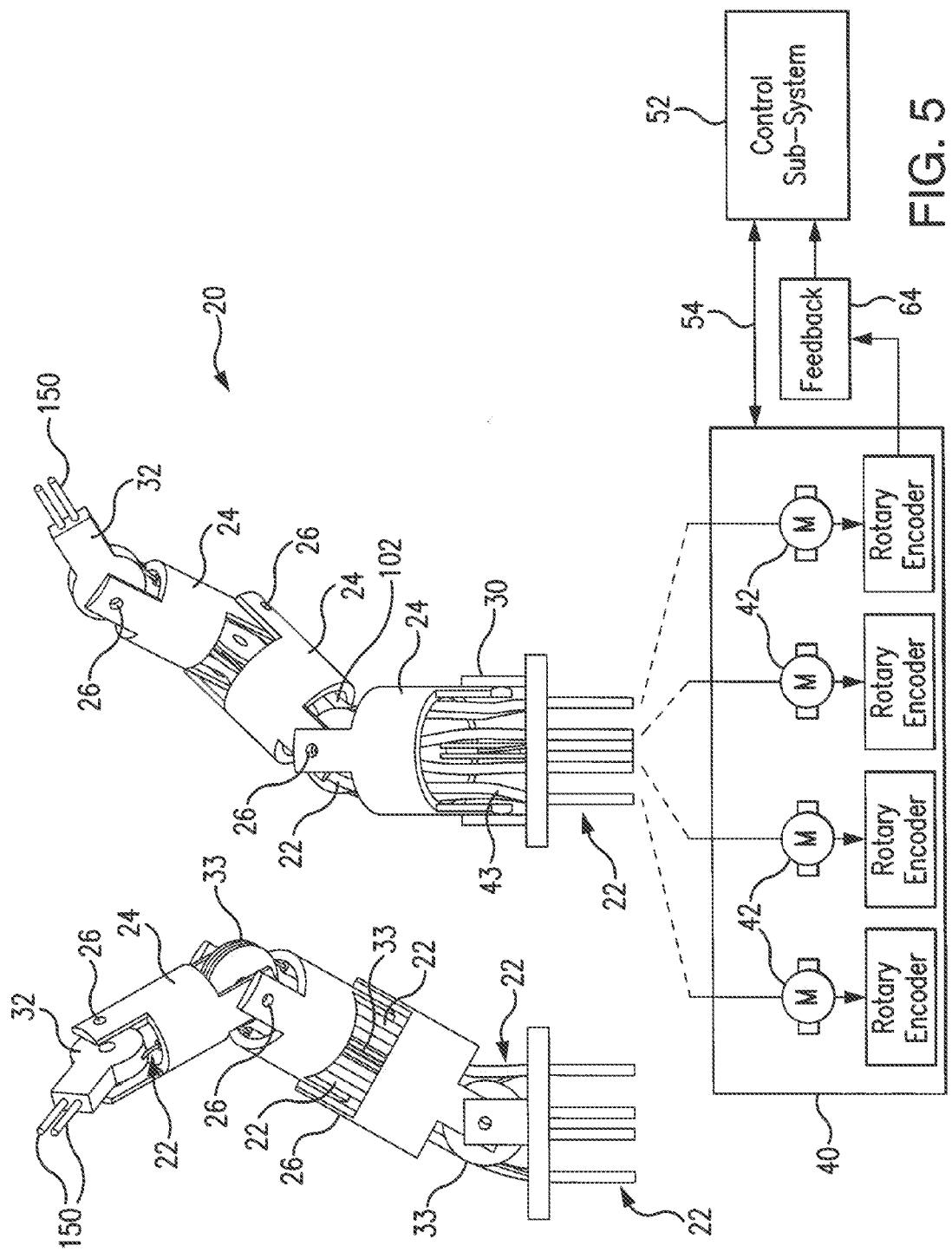

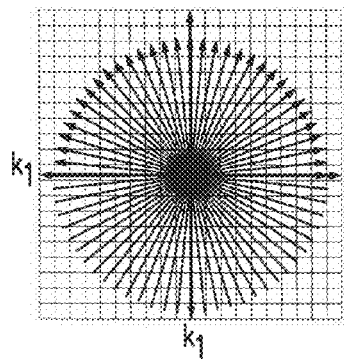
Increased number of projections for high resolution images and longer acquisition
FIG. 10A
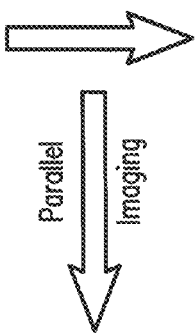
Parallel Imaging
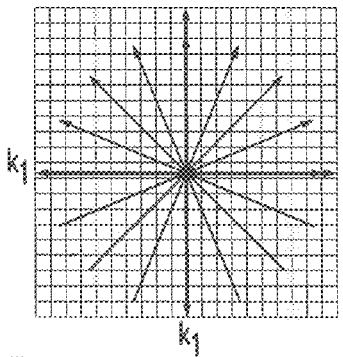
Fewer projections with parallel imaging to provide similar resolution with a short acquisition time
FIG. 10B
Standard (Sum of squares) 16 projections
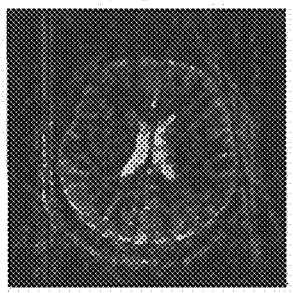
FIG. 10C
8x Accelerated 16 projections
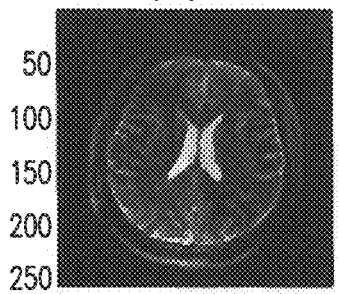
FIG. 10D
Reference 128 projections
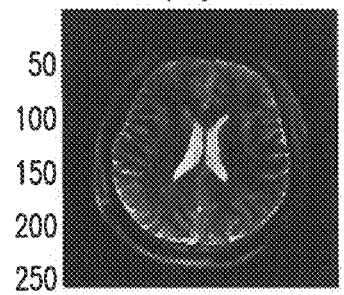
FIG. 10E

REAL-TIME TRACKING AND NAVIGATION SYSTEM AND METHOD FOR MINIMALLY INVASIVE SURGICAL PROCEDURES

REFERENCE TO RELATED APPLICATIONS

This Utility Patent Application is based on the Provisional Patent Application Ser. No. 61/641,482 filed on 2 May 2012; and in a continuation-in-part of Utility patent application Ser. No. 13/763,284 filed on 8 Feb. 2013.

STATEMENT REGARDING FEDERALLY SPONSORED RESEARCH OR DEVELOPMENT

This invention was made with government support under Grant Nos. EB008713 and EB008796 awarded by NIH. The U.S. Government has certain rights in this the invention.

FIELD OF THE INVENTION

The present invention relates to minimally invasive surgical procedures, and in particular to a robotic system for minimally invasive surgery.

More in particular, the present invention relates to a minimally invasive surgical procedure where a miniature surgical device is introduced to an operation site through a surgical corridor and teleoperatively guided by a surgeon based on the images of the operation site acquired substantially in real-time from an imaging system and the visual data acquired through a tracking system which enables the localization of the surgical device.

The present invention also relates to a real-time imaging technique that is designed for tracking end-effectors (catheters, microbots, etc.) in the operative site and for determination of a path for reaching a target of interest at the operational site for efficient biopsy sample retrieval or for therapeutic intervention, such as, for example, surgical tissue resection.

Additionally, the present invention relates to a minimally invasive surgical technique using the ability of a conventional MRI (Magnetic Resonance Imaging) scanner to function as a dynamic and flexible real-time interventional imaging tool and to provide real-time positioning information and image guidance.

Further, the present invention relates to a minimally invasive surgical system using a high dexterity miniature robot equipped with an end-effector (or end-effectors) which can be teleoperatively controlled by a surgeon to perform a surgical procedure facilitated by the real-time imaging guidance sub-system.

In addition, the present invention is directed to an automatic minimally invasive surgical system cooperating with an MRI sub-system and equipped with a sensor technology that uses signals from MRI gradient pulses for accurate determination of the position of a surgical device, and which is configured for dynamically tracking the end-effector and predicting the next scan frame location based on the surgical device trajectory history in order to attain continuous visualization of the operative site during the surgical procedure.

More in particular, the present invention is related to a miniature robotic sub-system integrated with an image-guided tracking sub-system and navigated teleoperatively by a surgeon to reach a target of interest based on integration of the images obtained from an imaging sub-system and the tracking information acquired by the tracking sensors for localization of the robot sub-system position. The robot sub-system may be provided with suction and irrigation channels within the robot structure and treatment tools (end-effectors) for tissue biopsy and/or removal, including, but not limited to one or more of the following: monopolar electrocautery, bi-polar electrocautery, laser ablation, radio-frequency ablation, ultrasonic cavitator, APC (Argon-Plasma Coagulation), catheter, microbots, etc., that may be employed in various imaging scenarios including, but not limited to the MR imaging.

Moreover, the present invention is directed to a minimally invasive surgical system which uniquely combines the tracking ability of the Endoscout® sensor(s) (from Robin Medical Systems) to acquire information on the location and/or orientation of the surgical device and to provide real-time imaging information to guide the surgical device to the target of interest in the most efficient and accurate fashion.

The present invention is further directed to a minimally invasive surgery using an interventional device which may be in the form of a miniature robot with out-of-plane motion capability. The interventional device is fabricated from a material compatible with the MR imaging technique and controlled by a surgeon.

Additionally, the present invention relates to a minimally invasive surgical robot which may be used with a number of imaging techniques including, but not limited to MRI (Magnetic Resonance Imaging), provided the components of the robotic sub-system are compatible with the particular imaging modality.

BACKGROUND OF THE INVENTION

Brain tumors are among the most deadly adult tumors and account for approximately 2% of all cancer deaths in the United States. The primary reason for the high mortality rate includes the inability to remove the complete tumor tissue due to the location of the tumor deep in the brain, as well as the lack of a satisfactory continuous imaging modality for intra-operative intracranial procedures.

Surgical resection of the tumor is considered the optimal treatment for many brain tumors. To minimize the trauma to the surrounding brain tissues during surgical resection, endoscopic port surgery (EPS) was developed, which is a minimally-invasive technique for brain tumor resection which minimizes tissue disruption during tumor removal.

However, due to the lack of satisfactory continuous imaging modality, it is extremely challenging to remove brain tumors precisely and completely without damaging the surrounding brain tissue using traditional surgical tools. As a result, patients may develop hemi paresis, cognitive impairment, stroke or other neurological deficits due to the procedure.

MRI (Magnetic Resonance Imaging) provides excellent soft-tissue contrast and the ability to distinguish the tumor margins, which enables a neurosurgeon to perform the procedure with less trauma to surrounding tissues during tumor resection. However, due to the strong magnetic field required for the MRI to operate commonly used sensors and actuators in conventional robotic systems are precluded from being used in MRI-compatible robots.

Several MRI-compatible surgical robotic systems have been designed in recent years. For example, Masamune, et al. ("Development of an MRI-compatible needle insertion manipulator for stereotactic neurosurgery", *J. of Image Guided Surg.*, 1995, 1(4), pp. 242-248) developed an MRI-compatible needle insertion manipulator dedicated to neurosurgical applications using ultrasonic motors; Wang, et al. ("MRI compatibility evaluation of a piezoelectric actuator system for a neural interventional robot", In Proc. IEEE Eng.

Med. Biol. Soc. Annu. Int. Conf., 2009, pp. 6072-6075) built an MRI-compatible neural interventional robot using a piezoelectric actuator system.

Kokes, et al. ("Towards a teleoperated needle driver robot with haptic feedback for RFA of breast tumors under continuous MRI", *Med. Image Anal.*, 2009, 13(3), pp. 445-455) developed an MRI-compatible needle driver system for Radio Frequency Ablation (RFA) of breast tumors using hydraulic actuation.

Yang, et al. ("Design and control of a 1-DOF MRI-compatible pneumatically actuated robot with long transmission lines", *IEEE/ASME Trans. Mechatron.*, 2011, 16, pp. 1040-1048) presented a design and control of an MRI-compatible 1-DOF needle-driver robot using pneumatic actuation with long transmission lines.

Fischer, et al. ("MRI-compatible pneumatic robot for transperineal prostate needle placement", *IEEE/ASME Trans. Mechatron.*, 2008, 13(3), pp. 295-305) developed an MRI-compatible robot for prostate needle placement using pneumatic actuation.

Krieger, et al. ("Design of a novel MRI compatible manipulator for image guided prostate interventions", *IEEE Trans. Biomed. Eng.*, 2005, 52(2), pp. 306-313, and "Development and preliminary evaluation of an actuated MRI-compatible robotic device for MRI-guided prostate intervention", In Proc. IEEE Int. Conf. Robot. Autom., 2010, pp. 1066-1073) developed an MRI-guided manipulator for prostate interventions using shaft transmission and piezo-ceramic motors.

Although the above-mentioned robotic systems are MRI compatible, they unfortunately cannot be used to reach a target which is not in the "line-of-sight" due to limited Degrees Of Freedom (DOF) of the robots intended for use in their systems.

N. Pappafotis, et al. ("Towards design and fabrication of a miniature MRI-compatible robot for applications in neurosurgery", in Int. Design Eng. Technical Conf. & Computers and Information in Eng. Conf., 2008) described a preliminary prototype of Minimally Invasive Neurosurgical Intracranial Robot (MINIR) using Shape Memory Alloy (SMA) wires as actuators.

An improved design of MINIR was proposed by Ho, M. and Desai, J. P. ("Towards a MRI-compatible meso-scale SMA-actuated robot using PWM control", in Int. Conf. on Biomedical Robotics and Biomechatronics, 2010, pp. 361-366) which improved several limitations of previous prototypes. The improved MINIR had individual SMA actuators for each joint. All joints were located on the outside surface of the robot and all wiring and tubes were routed inside the robot, thus attaining a more compact and easier shielded robot.

M. Ho, et al. ("Towards a MR image-guided SMA-actuated neurosurgical robot," in *Proc, IEEE Int. Conf. Robot, Autoin.*, 2011, pp. 1153-1158; and "Toward a meso-scale SMA-actuated MRI-compatible neurosurgical robot," *IEEE Trans. Robot.*, 2012, Vol. 28, No. 1, pp. 213-222), presented an MRI-compatible minimally invasive neurosurgical intracranial robot (MINIR) using SMA wires as actuators.

In M. Ho, et al. ("Towards a MR image-guided SMA-actuated neurosurgical robot", in proceedings of 2011 IEEE Int. Con. On Robotics and Automation, 2011, pp. 1153-1158), the force behavior of SMA (Shape Memory Alloy) actuators in the bent configurations was investigated.

Though the approach of using SMA (Shape Memory Alloy) wires as actuators was successful, there are significant limitations. Specifically, heating current has to be applied to the SMA wires while actuating the robot. The current can interfere with the magnetic field inside the MRI bore, and thus may lead to distortion in the image. Although the effects are limited and the profile of MINIR can be easily identified in the MR images, as presented in M. Ho, et al. ("Towards a MR image-guided SMA-actuated neurosurgical robot", in proceedings of 2011 IEEE Int. Con. On Robotics and Automation, 2011, pp. 1153-1158), the noise and distortion still causes difficulties in finding precise tumor boundaries.

It is clear that an improved surgical system for tissue biopsy, RF-ablation and other neurosurgical procedures involving tumor resection is needed in which the MRI noise is eliminated by using a real-time tracking and navigation technique which provides precise continuous virtual 3-dimensional visualization of the dynamical changes of the target during the surgery, and which aids in early detection of intratumoral hemorrhaging which may occur during resection, as well as in keeping track of shifting margins of the tumor during the surgical process, thus reducing potential complications of the surgery.

SUMMARY OF THE INVENTION

It is therefore an object of the present system to provide an automatic system for minimally invasive image guided surgical procedures that are teleoperatively controlled by a surgeon in a highly efficient and precise manner, designed with the goal of improving surgery outcome.

It is another object of the present system to provide a minimally invasive surgical system which is designed with a miniature surgical device sub-system operatively integrated with a real-time image tracking and guidance sub-system, which interfaces with the imaging sub-system, and generates tracking information corresponding to the real-time surgical device sub-system position information integrated with continuous visualization of the 3-dimensional shape changes of the target (tumor, neoplastic and non-neoplastic masses, etc.).

It is an additional object of the present system to provide a minimally invasive surgical robotic system with a miniature surgical device which is highly compatible with an imaging (MRI) modality used for the surgery and which is teleoperatively navigated by a surgeon in an intraoperative imaging modality environment based on the visual information available to the surgeon in the form of frequently updated MR images of the operative area of interest, where an accurate determination of the end-effector position and continuous virtual visualization of the procedure are obtained based on the signals from MRI gradient pulses and determination of the next scan frame of interest.

It is a further object of the present system to provide a minimally invasive surgical navigation system fully compatible with the MRI (Magnetic Resonance Imaging) technique where the MRI noise and distortion are eliminated through a controllable navigation of the surgical device based on tracking information and the images of the operative site. This attains dynamic acquisition of precise boundaries of tumors, both neoplastic and non-neoplastic masses, such as blood clots, as they change during the procedure, which is highly beneficial for a successful surgical procedure.

It is another object of the present system to provide a minimally invasive image-guided surgical system in which a miniature surgical robot is introduced to the operative site through a flexible cannula inserted by a surgeon through a narrow surgical corridor and which is teleoperatively steered by the surgeon by controlling the robot body in the most ergonomical and compact manner based on the real-time images and the end-effector tracking virtualized on a screen of the surgeon's interface.

It is still another object of the present system to provide a minimally invasive image-guided surgical robot system integrated with a tracking system, to facilitate the mechanism for tissue removal, and suction and irrigation tubes routed through a robotic system.

In one aspect, the present system is a system for telemetrical control of an interventional device for minimally invasive surgical procedure, which is based on principles which use real-time imaging for tracking a surgical device introduced in the operative site and determining a path for reaching a target of interest in the most accurate and effective manner for performing therapeutical and/or surgical procedure.

The system includes:

an imaging sub-system operated to produce substantially in real-time, images of an operative site comprising a target of interest;

an interventional device disposed at the operative site; and a tracking sub-system operatively coupled to the imaging sub-system, wherein the tracking sub-system is configured to produce tracking information corresponding to a location of the interventional device within the operative site.

The subject system further includes a navigation sub-system operatively coupled to the tracking sub-system, the imaging sub-system, and the interventional device. The navigation sub-system is preferably configured to:

(a) integrate the tracking information acquired by the tracking sub-system with the substantially real-time images produced by the imaging sub-system to generate coordinates of the interventional device in the operative site, (b) display the substantially real-time images of the operative site generated by the imaging sub-system, and (c) interconnect with a user to receive commands from the user to telemetrically control the interventional device, based on the substantially real-time images and the tracking information to reach the target of interest for an intended interaction therewith.

The system further includes a control sub-system operatively coupled to the navigation sub-system and the interventional device. The control sub-system is configured to generate control signals responsive to the user's commands input into the navigation sub-system and to apply the control signals to the interventional device to control its motion relative to the target of interest.

The tracking sub-system includes a sensor sub-system integrated with the interventional device, where the sensor sub-system includes at least one (or more) passive magnet field sensor (PMFS) positioned in proximity to a tip of the interventional device. Preferably, the sensor sub-assembly includes at least one (or more) second PMFSs positioned at a predetermined location along the length of the interventional device.

The imaging sub-system generates images based on imaging pulse sequences. The tracking sub-system uses predetermined tracking gradient pulses embedded in the imaging pulse sequences to induce currents in the sensor sub-assembly. The induced currents are processed to determine the position and orientation of at least one PMFS (or PMFSs).

The system uses pre-calibrated maps of induced currents corresponding to the sensor location within the imaging sub-system. The navigation sub-system is configured to correlate the induced currents from the PMFS to a corresponding location in the pre-calibrated maps.

The navigation sub-system is further configured to process substantially in real-time the coordinates of the individual PMFS, to compute coordinates of a next imaging slice, based on the specific PMFS coordinates, and to update dynamically, in real-time, the next imaging slice location during the surgical procedure. The navigation sub-system communicates the coordinates of the next imaging slice to the imaging sub-system substantially in real-time for the next image taking.

The system further includes an image acquisition sub-system operatively coupled to the navigational system to perform image reconstruction of the images. The image acquisition sub-system may use a real-time under-sampled projection reconstruction routine based on golden ratio projection ordering or use random sparse k-space sampling as well as available parallel imaging techniques to image the operative site.

The subject system operates in a tracking imaging mode or in a high resolution, a.k.a., a spot imaging mode. The navigation sub-system is further configured to adjust the acquisition needed for the high-resolution or the tracking mode of operation. Seamless transition from tracking to spot imaging is provided using the same MRI pulse sequences.

The tracking sub-system utilizes unique MR pulse sequences tailored for the surgical device sub-system to generate reliable real-time tracking coordinates for feed-back to the Imaging sub-system (Scanner) for obtaining images in the desired plane. This information may be used for tracking or to obtain high-resolution images.

The interventional device may be in the form of a minimally invasive robotic sub-system compatible with the imaging sub-system. The robotic sub-system for minimally invasive surgical procedures preferably includes an end-effector (or end-effectors) suitable for the intended interaction with the target of interest, which is actuated telemetrically by the user (surgeon) once the interventional device reaches the target of interest. The end-effector(s) may be adapted for tissue biopsy or tissue liquefaction of the target of interest.

The navigation sub-system constitutes an interface which is operatively interconnected between the surgeon and the interventional surgical device sub-system to provide the surgeon with a tool to telemetrically manipulate the surgical device sub-system based on real-time images and tracking information in order to reach the target of interest (tumor) for an intended procedure, for example, tissue liquefaction procedure, or tissue biopsy.

The tracking sub-system may comprise an Endoscout® sensor technology integrated with the surgical device sub-system and operatively coupled to the Navigation sub-system. The Endoscout® tracking sub-system includes a first Endoscout® sensor integrated with the interventional surgical device body and positioned at the surgical device's tip in proximity to the end-effector. An Endoscout® data processing unit is positioned externally of the operative area with the Endoscout® wiring extending internally through the surgical device body between the first Endoscout® sensor and the Endoscout® data processing unit positioned outside the imaging site. The Endoscout® tracking sub-system may further include a second (or third) Endoscout® sensor positioned along a length of the surgical device body, for example, at an end thereof opposite to the device's tip.

In particular, the present system permits interventional procedures to be performed in an MRI scanner sub-system under real-time guidance including accurate tracking of the surgical device location to allow the imaging to dynamically follow the interventional end-effector.

The system may be implemented with:

an MRI scanner,

Scanner Host PC that is operated by an MR technologist to control the MRI scanner, Device Host PC coupled to the surgical device sub-system to perform the intended intervention, Tracking Host PC that receives the tracking information of the end-effector(s) location from the sensor on the body of the surgical device inside the MRI scanner; and Navigation Host PC receiving and displaying images from the MRI scanner, and configured to integrate feedback from the Tracking Host PC with the MR images, and to issue commands to control the movement of the surgical device via the Robot Host PC. The Navigation Host PC is operated by a surgeon to perform a required procedure. The Navigation Host PC integrates feedbacks from various sources (MR imaging, Endoscout® position tracking, and feedback from the surgical device hardware), and provides the surgeon with a flexible interface to guide the surgical device. The surgeon may use the interface to advance the surgical device by using remote controls on a Graphical User Interface (GUI).

The surgical device may be implemented, for example, as a minimally invasive robot sub-system with out-of-plane motion capability.

A control sub-system is operatively coupled between the surgeon's interface (Navigation sub-system) and the interventional device sub-system. The control sub-system generates control signals responsive to the surgeon's commands entered via the interface and transmits the control signals to an actuator sub-system of the interventional device. The actuator sub-system, responsive to the control signals received, controls displacement of the interventional device parts, thereby steering the robot sub-system relative to the target of interest.

The interventional device is equipped with one (or more) end-effector(s) adapted for intended interaction with the target, such as for example, tumors, both neoplastic and non-neoplastic masses, such as blood clots. Preferably, the end-effector(s) is (are) electrically coupled to end-effector hardware through wiring.

The end-effector(s) is (are) adapted for tissue liquefaction of the tumor, and may be selected from a number of techniques, including but not limited to one or more of the following: monopolar electrocautery, bi-polar electrocautery, APC (Argon-Plasma Coagulation), laser ablation, radio-frequency ablation, ultrasonic cavitation, etc. The end-effector(s) also may be in the form of a catheter adapted for tissue biopsy.

The robot sub-system is equipped with a visual feedback control between the Endoscout® sensors and the control sub-system. The visual feedback control is based on the tracking information acquired from the tracking system.

The control sub-system further includes a processor controlled data transformation unit receiving the surgeon's commands. It calculates corresponding control signals based on the position and configuration of the robot body. The control signals include coordinates of the interventional device (or parts thereof), and tracking path interpolation. The control signals are operatively coupled to the actuator sub-system to control the motion of the robot body.

In addition, the system contemplates to acquire a feedback data from the interventional device, and combine that feedback data with the tracking information and the imaging data to facilitate performance of the system in question.

In another aspect, the present system is directed to a method for telemetrically controlling an interventional device during a surgical procedure. The method includes the steps of:

integrating a tracking sensor sub-system with an interventional (surgical) device adapted for a surgical procedure;

positioning an operative site containing a target of interest into an imaging sub-system;

introducing the interventional device to the operative site containing the target of interest; and operatively coupling a navigation sub-system to the tracking sensor sub-system, the interventional device, and the imaging sub-system.

The method is further enhanced with the steps of:

configuring the navigation sub-system to display substantially real-time images acquired from the imaging sub-system;

integrating the substantially real-time images with tracking information obtained from the tracking sensor sub-system, and generating coordinates of the tracking sensor sub-system in the operative site; and upon receipt of a command from a user to move the interventional device, issuing a control signal applied to the interventional device to actuate a required section relative to the target of interest for an intended surgical interaction.

The method provides the steps of:

generating images in the imaging sub-system in correspondence to predetermined imaging pulses sequences, embedding pre-determined tracking gradient pulses in the imaging pulses sequences, inducing currents in the tracking sensors sub-systems by the tracking gradient pulses, and processing the induced currents to determine a real-time position of the tracking sensor sub-system.

The method is enhanced by performing the steps of:

optimizing the imaging pulse sequences by:

embedding the tracking gradient pulses in the format of calibrated bipolar pulses having a predetermined duration and strength, and using a frame rate of image acquisition exceeding the time duration requirement for obtaining a single projection.

The method further includes the steps of:

computing in real-time, the coordinates of the tracking sensor sub-system, computing in real-time, coordinates of a next imaging slice based on the coordinates of the tracking sensor sub-system, updating in real-time the imaging slice location during the surgical procedure, and actuating the imaging sub-systems accordingly.

During the surgery, the surgeon may obtain high-resolution diagnostic quality images of the operative area when needed. The method further includes the steps of:

operatively coupling an image-acquisition sub-system to the navigation sub-system, performing image reconstruction using golden ratio projection ordering, or using random sparse k-space sampling to minimally depict the operative site during tracking, and adjusting the number of projections needed for a high resolution imaging mode or tracking imaging mode of operation with various contrast (T1 or T2-weighted).

The subject method constitutes a technique for real-time tracking and navigation of a surgical device for reaching a target of interest for an efficient minimally invasive surgical procedure.

The subject method is enhanced by providing the tracking sub-system with at least one (or more) sensor(s) which is (are) positioned in proximity to the end-effector(s) and/or along the length of the surgical device's body to generate tracking information corresponding to a position of the end-effector(s) or any other point of interest on the surgical device;

introducing the surgical device to an operative area of a patient, exposing the operative area to an imaging routine;

producing MR coordinates corresponding to the location of the end-effector based on the tracking information, obtaining real-time images of the area containing the target of interest (tumor, etc.) on a display of a neurosurgeon's interface;

integrating the tracking information (in the form of the coordinates) acquired from the tracking sub-system and the real-time images of the operative area on the display of the operator's interface; and prompting the surgeon, through the surgeon's interface, to control the surgical device position based on the tracking information and the real-time images by entering the surgeon's commands via the surgeon's interface.

Responsive to the surgeon's commands, the procedure continues through the steps of:

calculating and operatively applying control signals to the surgical device to navigate the surgical device relative to the target of interest to perform a required surgical and/or therapeutical procedure by the end-effector.

The subject method is enhanced through determining, in real-time, the position of the next scan slice (frame) of the operational site for imaging based on the tracking information. The position of the next scan slice is communicated to the imaging scanner for taking the image. This approach permits continuous virtual visualization of the surgical procedure.

The method further includes the steps of equipping the surgical device with an additional tracking sensor positioned at a predetermined spot along its length. The navigation sub-system is configured to track all sensors seamlessly to assist in accurate tracking of the surgical device.

Further operations of the subject method are carried out through the steps of:

coupling a surgical device control sub-system to the navigation sub-system for controlling the motion of the surgical device, receiving, at an input of the control sub-system, the surgeon's commands, computing corresponding control signals based on the position and configuration of the surgical device, applying the control signals to the surgical device (specifically, to an actuator sub-system of the surgical device sub-system) to control motion of the end-effector relative to the target, and carrying out a visual feedback control between the tracking sub-systems and the Navigation sub-system.

The actuator sub-system's feedback may be acquired and combined with the tracking information and the imaging data to be used for enhancement of the performance of the system, thus potentially resulting in improved safety of the surgical procedure.

These and other features and advantages of the present invention will be apparent from the following detailed description taken in conjunction with accompanying patent drawings.

BRIEF DESCRIPTION OF THE DRAWINGS

FIG. 5 illustrates the robot body operatively coupled to the actuator sub-system designed with motor actuators;

FIGS. 10A-10E illustrate principles of the parallel imaging applied to image acquisition in the present method.

DESCRIPTION OF THE PREFERRED EMBODIMENTS

The ability of a conventional MRI (Magnetic Resonance Imaging) scanner to function as a dynamic, flexible real-time interventional imaging tool is appealing as closed-bore systems become more open and accessible. While available MRI techniques can rapidly acquire images, there is currently no reliable way to accurately position and control a robotic system to perform biopsies (or other surgical procedures) within an MRI scanner. The subject robotic system operates within a closed-bore MRI scanner, and provides real-time positioning information and image guidance using a passive magnet field sensor (PMFS).

Although the principles of the present system and method are applicable to a number of minimally invasive surgical procedures, the following description, as an example only, but not to limit the applicability and scope of the invention to any particular implementation, will be presented with reference to a neurosurgical procedure performed with the assistance of an imaging technology and supported by real-time tracking and telemetrical navigation of an end-effector relative to the target of interest for effective and precise procedure with the goal to reduce (or eliminate entirely) complications from therapeutic intervention.

Figure 1:
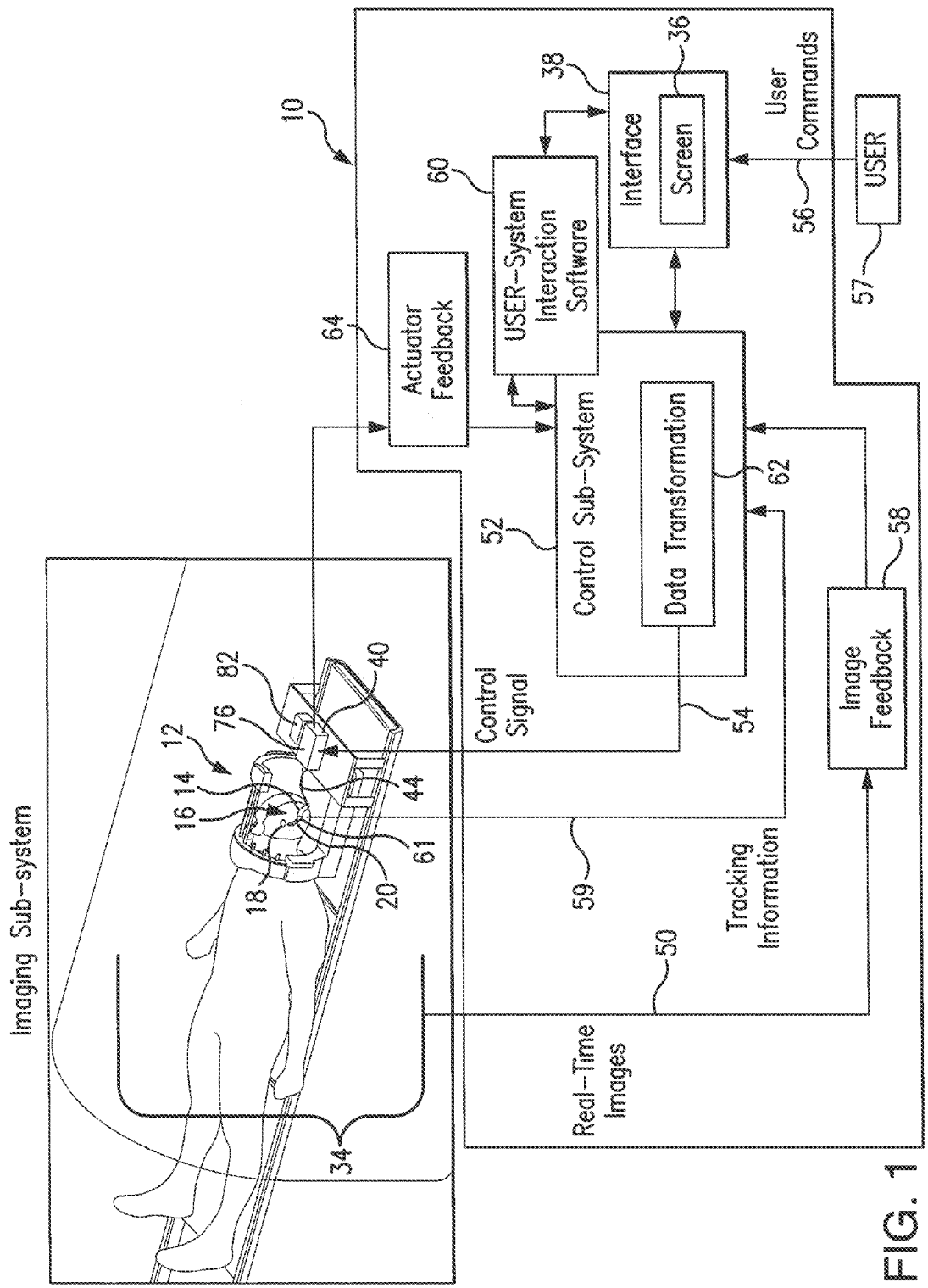
FIG. 1 is a block diagram representing, in simplified form, the surgical setup using the present minimally invasive surgical robotic system.
Figure 3:
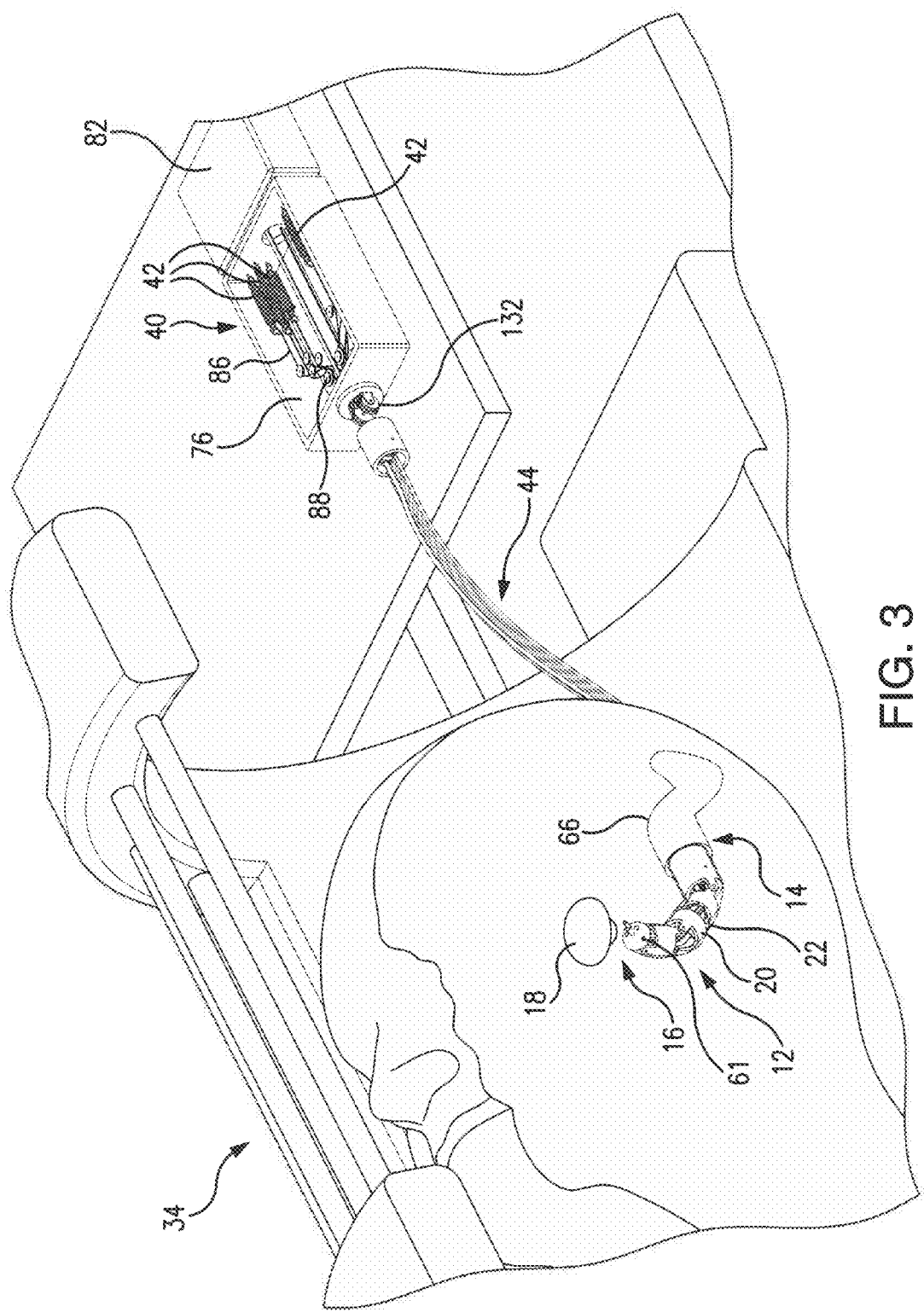
FIG. 3 is a representation of the robot sub-system of the present invention introduced into the operative site through a surgical corridor.

Referring to FIGS. 1 and 3, a real-time tracking and navigation system 10 may operate in conjunction with a surgical device 12, which may be preferably any minimally invasive miniature device applicable to an interventional procedure, permitting out-of-plane motion, and be compatible with the imaging technology used for the interventional procedure in question.

As an example, the surgical device 12 will be described, for example, as a minimally-invasive neurosurgical intracranial robot sub-system 12, which during the surgery is introduced through a narrow surgical corridor 14 to an operative site 16 containing a tumor 18.

The present system enables the neurosurgeon to remove deep brain intracranial tumors, both neoplastic and non-neoplastic masses, such as blood clots, that are typically hard to reach through a minimally invasive approach, since deep brain tumors are typically located away from the "line-of-sight" of the neurosurgeon.

The present system provides the neurosurgeon with means to remove the tumor by teleoperatively navigating the position of the minimally invasive neurosurgical intracranial robot which has a number of DOFs (Degrees-of-Freedom) towards the tumor site based on real-time images of the operational site integrated with visual tracking data of the robot, as will be presented in detail in following paragraphs.

Figure 4:
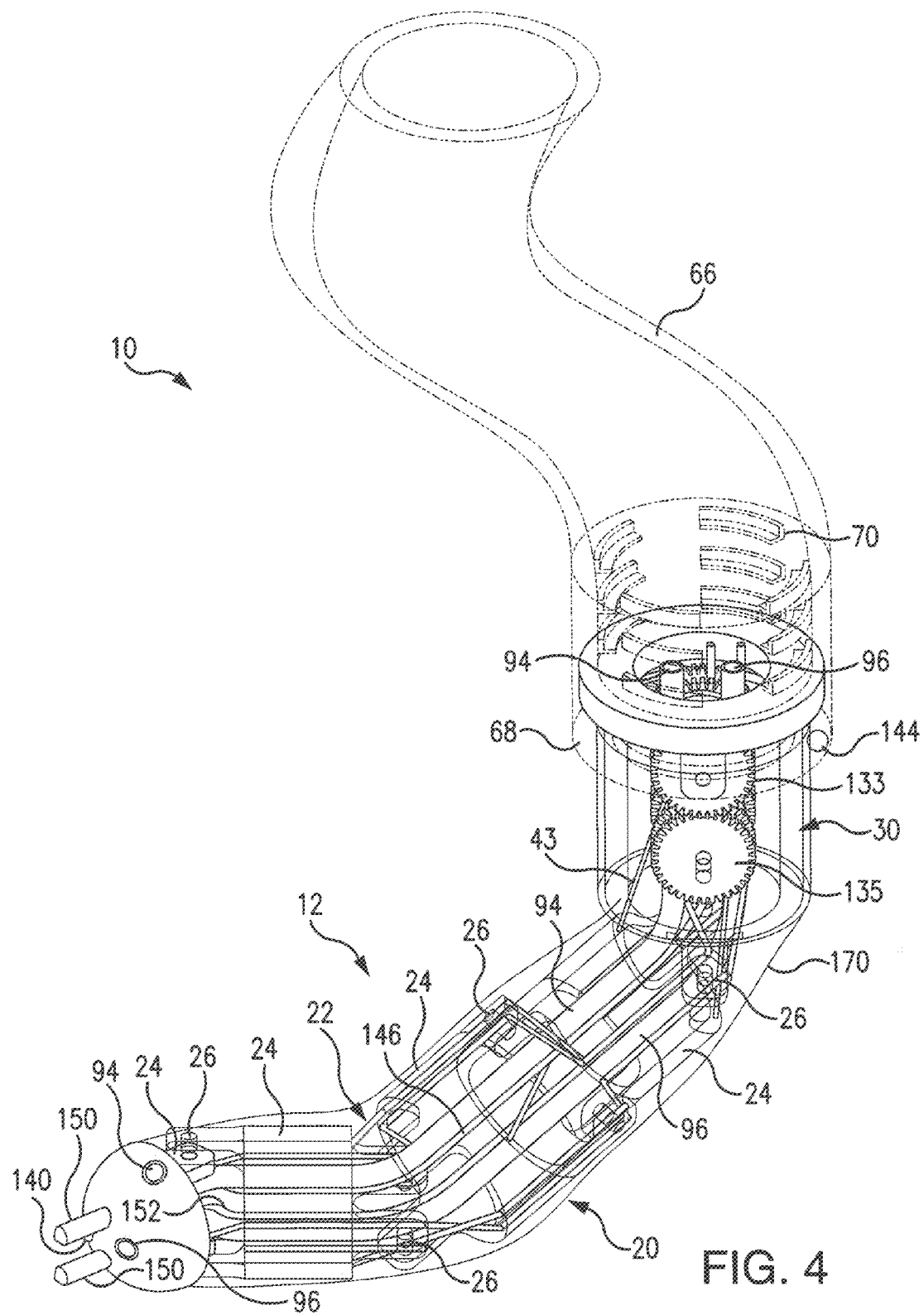
FIG. 4 is a pictorial representation of the robot sub-system latched at the end of a cannula.

As shown in FIGS. 3-5, the exemplary robot sub-system 12 includes a robot body 20 and a tendon sub-system 22 fully integrated with the robot body 20 and routed through the robot body 20 in a predetermined fashion.

The robot body 20 may be composed of a plurality of links 24 interconnected through revolute joints 26. Each revolute joint 26 is formed between adjacent links 24 for rotational motion of each link with respect to the other about a corresponding rotational axis. Each axis extends in substantially orthogonal relationship with an adjacent axis to provide the "out-of-plane" motion for the links.

The number of the links is not limited and may vary depending on the specific surgical operation to be performed. The links include a base link 30 and a tip link 32, and several intermediate links connected therebetween.

The system 10 operates in conjunction with an imaging system 34 which generates substantially real-time images of the operative site 16 containing the tumor 18 and provides these images to the screen (or any other display mechanism) 36 on the neurosurgeon's interface 38.

The principles of the present system are fully applicable to a variety of imaging modalities. In order to be used with a particular imaging system, such as, for example, MRI, the robot sub-system 12 is adapted to be compatible with the particular imaging modality. Different imaging modalities may be incorporated using real-time image fusion techniques.

As an example, the following description is given for the system operated in an intraoperative MRI (Magnetic Resonance Imaging) environment, which uses the ability of a conventional high-field MRI scanner to function as a dynamic, flexible real-time interventional imaging tool to accurately position and control a robotic system to perform biopsies (or other surgical procedures) within the MRI scanner.

The interventional device sub-system is envisioned to be under the direct control of the neurosurgeon with the targeting information obtained from frequently-updated MRI images which are used to provide virtual visualization of the operative site containing the tumor as the tumor's 3-dimensional shape changes during the surgery.

For example, when being used with the MRI, all the components of the robot body sub-system 12 will be manufactured with MRI compatible materials to attain minimal or no distortion in Magnetic Resonance Images. In the embodiment compatible with the MRI technology, links are made of a plastic, or MRI compatible metals, such as, for example, brass, titanium, etc., and tendon sub-system 22 will contain cables (tendons) routed through sheaths. As an example, the tendons and sheaths can be made from plastic or MRI compatible components.

Referring again to FIG. 1, the system 10 includes an actuator sub-system 40. As shown in FIGS. 3 and 5, the actuator sub-system 40 includes independent actuating mechanisms 42, the number of which corresponds to the number of revolute joints in the robot sub-system 12. Each actuating mechanism 42 is operatively coupled to a respective revolute joint 26 in the robot body 20 through a particular tendon 43 (as shown in FIG. 5) in the tendon sub-system to control the revolute motion at each particular joint.

Several embodiments of the actuator sub-system 40 are envisioned herein. However, irrespective of its nature, each actuating mechanism 42 independently controls the joint motion of one corresponding joint 26 in a desired direction by controlling the motion of a respective tendon 43 in the tendon sub-system 22.

While MRI provides an extremely restrictive environment when it comes to material, sensors, actuators, etc., choices that can be used, some of these constraints are not present in other imaging modalities, such as, for example, CT and ultrasound. In any case scenario, the actuator sub-system 40 is preferably positioned away from the imaging system to reduce (or completely eliminate) image distortion. In order to reduce (or completely eliminate) the noise and distortion to the images which may be caused by operation of the actuator sub-system 40, the actuator sub-system is positioned in spaced apart relationship with the imaging system 34.

The operative coupling between the actuator sub-system 40 and the tendon sub-system 22 in the present design may be provided through an intermediate quick-connect mechanism 44 (shown in FIG. 3), the proximal end of which is attached to the actuator sub-system 40, while the distal end is attached to the robot base link. The intermediate quick-connect mechanism 44 includes cabling (tendons) passing through plastic sheaths.

The tendons are pre-tensioned and are maintained in tension during the entire operation. All the tendons in the robot sub-system are in pre-tension immediately before the operation of the robot initiated. However, the tendons in the intermediate quick-connect mechanism 44 themselves are not pre-tensioned when they are not connected between the actuator box and the robot body or not in operation.

The plastic sheaths are used in the intermediate quick-connect mechanism 44 to route therethrough the wiring for the tracking sub-system (for example Endoscout® tracking system), as well as wiring for probes of surgical modalities, which may be used for a particular procedure intended to destroy the tumor tissues.

In addition, the intermediate quick-connect mechanism 44 may include tubes routed therethrough for suction and irrigation procedures provided at the robot sub-system 12 to enable the removal of the tissues when needed. For these purposes, respective ends of the suction and irrigation tubes are entered into contact with the operative site.

Returning to FIG. 1, the system 10 further includes a control sub-system 52 which is operatively coupled between the interface 38 and the actuator sub-system 40. The control sub-system 52 generates control signals 54 responsive to the neurosurgeon's commands 56 entered by the neurosurgeon (user) 57 into the interface 38. The control signals 54 generated by the control sub-system 52 are applied to the actuator sub-system 40, which, responsive to the control signals 54 received actuates a respective actuating mechanism 42 to control the motion of the tendons in the tendon sub-system 22. This causes rotational motion of the respective links at the revolute joints to steer the robot sub-system 12 towards the tumor 18 at the command of the neurosurgeon.

The control sub-system 52 calculates the center of rotation at the robot body, i.e., the coordinates of the joint to be affected, and actuates the actuating mechanism 42 corresponding to a joint to control the specific joint independently of others.

The neurosurgeon's instructions to steer the robot body 20 are based on the real-time MRI images 50 received at the screen 36 of the interface 38. In addition, the neurosurgeon is provided with the tracking information 59 acquired by the tracking sub-system 61 integrated with the robot body 20.

The tracking information 59 may be in the format of coordinates of the end-effector (or other part) of the robot.

An image feedback control sub-system 58 integrates feedbacks from various sources (MR imaging, tracking information from the tracking sub-system and feedback from the robotic sub-system hardware) and provides the neurosurgeon with the fluid interface to guide the robot sub-system 12 through the commands 56. In other words, based on the tracking information integrated with the MRI images at the screen 36 of the interface 38, the neurosurgeon monitors the efficiency of the teleoperative steering of the robot body's in a predetermined manner relative to the tumor during the surgical procedure.

The control sub-system 52 and the interface 38 operate in accordance with User-System Interaction Software 60 which supports the overall control process, as will be further presented. The control sub-system 52 further includes data processor 62 which transforms the neurosurgeon's commands 56 into the control signals 54. The data processor 62, responsive to the commands 56, calculates the center of rotation at the robot body 20, i.e., the coordinates of the revolute joint 26 to be actuated, as well as operational parameters for the actuating mechanisms 42 in the actuator sub-system 40 to affect the motion of the robot.

As presented in FIG. 3, the actuating mechanisms 42 may be implemented as SMA (Shape Memory Alloy) actuators. Alternatively, as presented in FIG. 5, the actuating mechanisms 42 may be implemented with motors.

In the case of the SMA actuators, the data processor 62 calculates a temperature to which the particular SMA actuator is to be heated, and the corresponding electrical current supplied thereto as will be further described.

In the case of employing motors for actuating mechanisms 42, the data processor 62 calculates the regime of the motor operation in order to provide a needed motion of particular cables in the intermediate quick-connect mechanism 44, and the motion of the corresponding tendons 43 of the tendon sub-system 22.

Specifically, the following modifications of the actuator design are envisioned in conjunction with the present system including, but not limited to, the SMA springs actuators, DC motors, or Piezo LEGS rotary motors (manufactured by PiezoMotor, Uppsala, Sweden), with a choice of the actuator sub-system 40 dependent on the choice of the imaging modality.

For example, if DC motors are used, each DC motor may be equipped with a rotary encoder (shown in FIG. 5) and a high gear ratio which is used to give the robot sub-system both fine motion and high output torque.

The number of the actuating mechanisms 42, either motor based or SMA spring based, corresponds to the number of the revolute joints in the robot sub-system to provide an independent control of the tendons and hence the joints 26. The number of degrees of freedom of the system automatically determines the number of actuating mechanisms.

The system 10 also includes an actuator feedback control sub-system 64, shown in FIGS. 1 and 5.

Referring to FIGS. 3 and 4, the robot sub-system 12 is delivered at the operative site 16 through a flexible cannula 66 which is inserted by the neurosurgeon into narrow surgical channel. The neurosurgeon advances the robot body 20 as much as it is required through the cannula 66 into the operative site 16. The cannula 66 is provided with a mechanism (for example, latching mechanism) 70 designed for securing the base link 30 at the distal end 68 of the cannula 66.

During the surgery, as shown in FIGS. 1 and 3, the neurosurgeon advances the robot body 20 to a position required for the procedure. The latching mechanism 70 enables the neurosurgeon to control the appropriate amount of the protrusion of the robot body through the cannula 66, and hence the depth to which the robot body protrudes into the brain.

Returning to FIGS. 1 and 3, the actuator sub-system 40 may be encased in the actuator box 76 which, in one embodiment, includes SMA antagonistic spring actuators coupled by one end to a hardware routing box 82 which contains the Endoscout®, electrocautery, suction, and irrigation hardware. An opposite end of the SMA springs is coupled through the cables 86 and through intermediate routing pulleys 88 to the gears 132 extending outside of the actuator box 76. The cables 86 routed through the intermediate routing pulleys 88 are in tension during the operation.

Each joint of the robot body is connected to a pair of antagonistic SMA spring actuators shown in FIGS. 1 and 3, which allow control of the joint motion in both directions independently.

When one of the spring is heated by applying electric current, the tension in the heated SMA spring increases as opposed to another non-heated SMA spring, thereby causing the joint motion in the direction of the heated SMA spring.

By applying electric current to a specific one of the springs in the SMA spring actuator, the spring cables 86 rotate (through the corresponding pulley 88) the gears 132 (shown in FIG. 3) in the direction corresponding to the heated/non-heated antagonistic springs.

In order to provide the transformation of the action of the actuating mechanisms 42 into controlled motion of the tendons 43 in the tendon sub-system 22 integrated with the robot body 20, a system of operating gear sets is provided in the robot sub-system.

The rotational motion of the gears 132 is transferred through the intermediate quick-connect mechanism 44 through the system of gears 133 (shown in FIG. 4) and a respective tendon 43 to a respective joint of the robot body to steer the robot as needed.

The gearing in the present system is provided for the motion and torque amplification as appropriate to the function of the system.

Thus, the actuation of a corresponding SMA spring is transformed (through the cables 86 and the pulleys 88) into rotation of a respective gear/pulley unit 132 which, in turn, is transformed into the controlled motion of a respective cable in the intermediate quick-connect mechanism 44 resulting in rotation of a gear/pulley unit in the set 133 which correspondingly rotates the gear/pulley in the set 135. Such rotation of the gear/pulleys sequentially results in the control of the motion of a corresponding tendon 43 routed through the robot body 20, thereby actuating a respective joint and causing rotational motion of one link with respect to the other in correspondence with the control signal 54 responsive to the neurosurgeon's command 56.

As seen in FIG. 4, the robot body 20 is a hollow body which permits routing of the suction tube 94, irrigation tube 96, as well as the wiring for probes and tracking system inside the robot body 20 thereby further promoting minimization of the robot dimensions.

Figure 2:
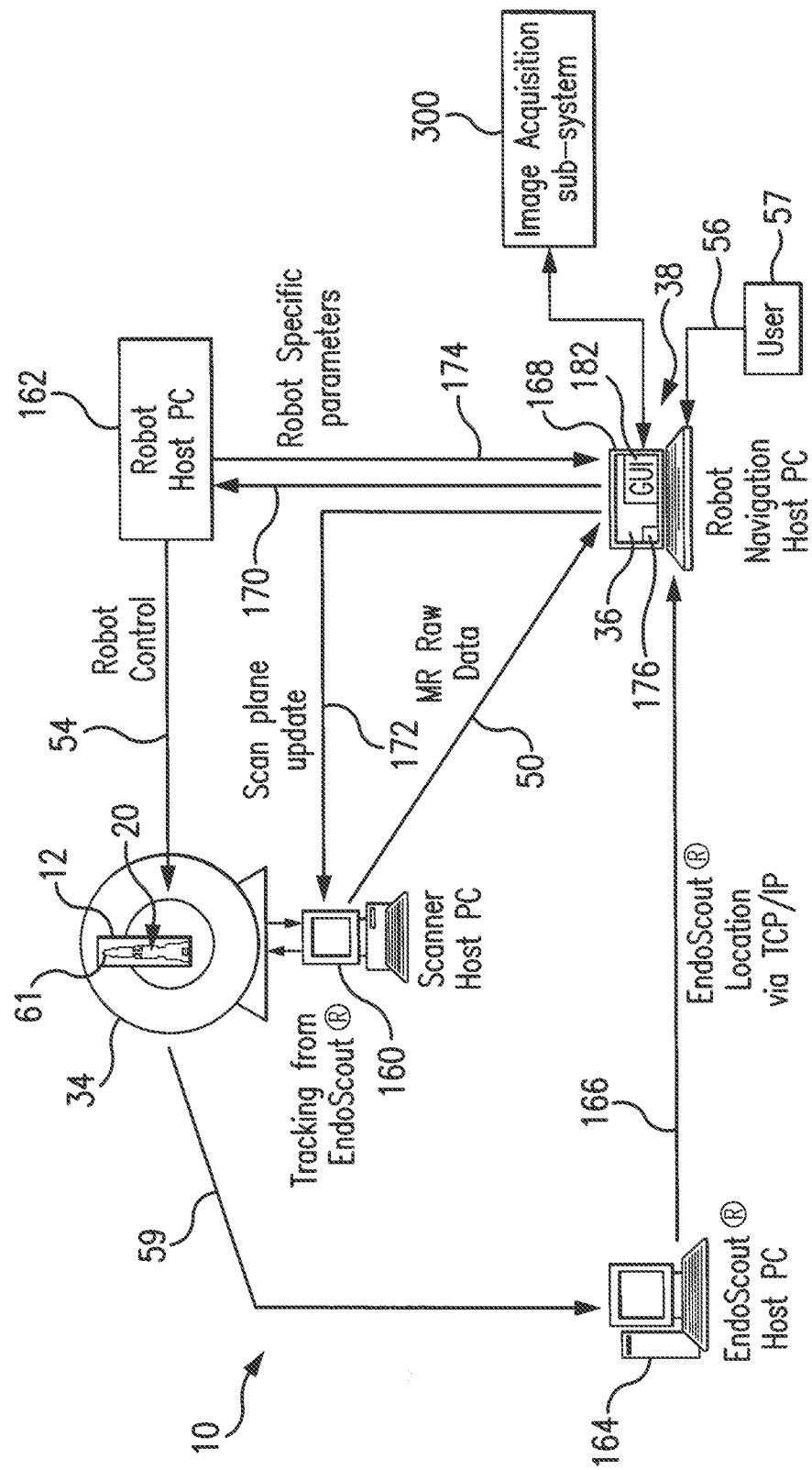
FIG. 2 is a block diagram representation of the present tracking and navigation system for minimally invasive surgery.

As shown in FIGS. 1-3, the robot sub-system 12 is integrated with the tracking sub-system 61 which may be one of a variety of tracking systems compatible with imaging technology used for medical purposes. For example, the present system may be equipped with the Endoscout® tracking system (manufactured by Robin Medical Inc.). The Endoscout® tracking system is a system for MRI guided interventions which enables tracking of the location and orientation of miniature sensors during the MRI scan. The tracking is based on the native gradient fields of the MRI scanner.

As shown in FIG. 4, in the present system, one Endoscout® sensor 140 is positioned at the hemispherical tip member 142. In addition, a second Endoscout® sensor 144 may be attached along the length of the robot body, for example, at the distal end 68 of the flexible cannula 66. The wiring 146 for the Endoscout® is routed inside the hollow body 20 of the robot from the sensors 140 and 144 along the intermediate quick-connect mechanism 44 to the hardware routing box 82. In one embodiment, the wiring 146 for Endoscout® system passes through the actuator box 76 for compactness of the system.

The hemispherical tip member 142 secured at the tip link 32 carries end-effector (probes, catheter, etc.) 150 to perform surgical procedures in a number of treatment modalities which may be used for a particular procedure for biopsy or to destroy tissues of the tumor. The wiring 152 for these treatment modalities extends inside the hollow robot body 20 from the probes 150 at the hemispherical member 142 to the hardware routing box 82. The routing of the wiring 152 may preferably be carried out along the intermediate quick-connect mechanism 44 and through the actuator box 76 for ergonomical benefits as well as compactness of the system 10.

Further attached to the hemispherical member 142 at the tip link 32 is the end of the irrigation tube 96 and suction tube 94 which are routed inside the hollow robot body 20 towards the hardware routing box 82 preferably along the intermediate quick-connect mechanism 44 and the actuator box 76. The suction and irrigation channels within the structure enable the treatment modality approach for removal of the tissue. The suction tube 94 is attached to a pump (not shown) at the end opposite to the end extending into the intracranial operative site to controllably remove tumor tissues. The irrigation tube 96 is connected to a liquid reservoir (not shown) to supply the irrigation liquid to the operative site when needed to clear blood and tissue debris.

FIG. 2 exemplifies one of the implementations of the communications between various components of the subject real-time tracking and navigation system 10. The present system allows interventional procedures to be performed in the MRI scanner 34 under real-time guidance including accurate tracking of the end-effector (biopsy needle, RF ablator, microbot, etc.) location to allow the imaging to dynamically follow the end-effector during the surgical (or any therapeutical) procedure.

As outlined in FIG. 2, the system 10 is composed of:

a Scanner Host PC 160 which is operated by an MR Technologist to control the MR scanner 34;

a Robot Host PC 162 which controls the movement of the robotic hardware via control signals 54 to perform the intervention procedure;

a Tracking (Endoscout®) Host PC 164 which receives the tracking information 59 from the tracking sub-system 61 integrated with the robot body 20; and a Navigation Host PC 168 which receives images 50 (such as for example MR raw data) from the Scanner Host PC 160, displays the received images 50 at the display 36, integrates feedback 166 from the Endoscout® Host PC 164, and issues commands 170 supplied to the Robot Host PC 162 to control the robot displacement. The Navigation Host PC 168 is operated by an Interventionalist 57 to perform the procedure. The images 50 are transferred from the MRI scanner (or the Scanner Host PC 160) via a standard Ethernet connection.

The present system is designed to be transparent to any customization of the MRI hardware.

In operation, the robot is guided by the interventionalist (surgeon, user) 57. The location of the robot is continuously tracked by the Endoscout® sensor(s) which in turn provides the location information 166 of the robot's end-effector to the Navigation Host PC 168. The Navigation Host PC 168 in turn uses the location information 166 to predict the next slice location based on its trajectory history which it communicates with the Scanner Host PC 160.

In an alternative implementation, it is contemplated that network delays are further minimized by incorporating the logic available in the Endoscout® Host PC 164 and the specific host PC of the device (if necessary) into the Navigation Host PC 168. The calibration file 176 may be provided for example in the Navigation Host PC 168 to transform the Endoscout® coordinates 166 to the MRI scanner coordinates 172.

Device tracking information 59 (and/or 166) is used for future slice prescription in real-time. Flexibility for operating in the tracking mode or in the high-resolution mode is provided to the Navigator Host PC interface by appropriately adjusting the number of projections needed for a given image. A single unified user interface on the independent Navigation Host PC 168 is developed that integrates information from both the Scanner Host PC 160 and the Endoscout® interface 164 to enable communication with the scanner 34, performing off-line reconstruction all within the confines of a Graphical User Interface (GUI) that permits easy visualization during tracking, analyzing high resolution images, and provides assistance in planning further intervention.

A standard Ethernet connection may be used to integrate the tracking information from the Tracking Host PC 164 to the Navigation Host PC 168 at a predetermined update rate for the scan plane.

In order to provide useful intervention and imaging, it is of importance to update the scan plane of the MRI scanner in near real-time. This approach permits imaging to track the location of the robot's end-effector (obtained through the Tracking sub-systems 61) without intervention from an operator.

The real-time update of MRI scan plane feature of the present system requires a customized MR pulse sequence to retrieve positional information corresponding to the scan plane update data 172 from the Navigation Host PC 168.

The tracking may be obtained in a variety of modes. For example, as one of the designs consideration, an induction pick-up coil may be used as a sensor which triangulates the sensor position to coordinates inside the MR scanner 34. Such systems are commercially available (e.g. Robin Medical Inc. Endoscout® system) and FDA approved.

As shown in FIG. 4, the tracking sub-system 61 includes the Endoscout® sensor 140 positioned in close proximity to the end-effector 150. Alternatively, to enhance the preciseness of the tracking and navigation, the tracking sub-system 61 may be also formed with another Endoscout® sensor 144 positioned at a predetermined location along the length of the robot body 20, for example, in proximity to the base link 30.

The Endoscout® Host PC 164, upon receipt of the tracking information 59 from the Endoscout® sensor(s) 140, 144, generates tracking data 166 for location(s) of the sensor(s) 140, 144 inside the MRI scanner.

The Endoscout® sensors 140 and 144 located at the tip 142 of the robot body 20 and at the distal end of the cannula 66, respectively (as shown in FIG. 4), transmit the tracking information corresponding to the position of the robot body to the Endoscout® Host PC 164, which in turn communicates the acquired information to the Navigation Host PC 168 which converts the coordinates of the sensors 140, 144 to the MR (Magnet Resonance) coordinates, i.e., integrates the tracking visual 166 with the MR images 50.

The Navigation Host PC 168 displays images 50 from the Scanner Host PC 160, integrates feedback 166 from the Endoscout® Host PC 164, and issues commands 170 to control the robotic hardware.

The robot body is driven through the tendons system controlled by actuators (either SMA or motors) as presented previously. Position and orientation of the robot is controlled by motioning various tendons in real-time. The robot is driven by network remote control, using standard Ethernet communication 170 with the Robot Host PC 162 from the Navigation Host PC 168. The Robot Host PC functions as a server to respond to surgeon's commands 56 to adjust position. The Navigation Host PC 168 receives a stream of coordinate updates 166 at a rate of 5-20 Hz.

The Navigation Host PC 168 functions as the "brain" of the intervention system. Its role is to integrate feedback from various sources (MR imaging 50, Endoscout® position tracking 166, and feedback 174 from the robotic hardware) and provide the Interventionalist with a fluid interface to guide the robot. It is designed to receive DICOM images from a shared network folder and display single and multi-slice data.

For phase-images, temperature maps may be generated using proton resonance frequency-based methods.

The Interventionalist (user, or surgeon) 57 uses the interface 38 to advance the robot by using remote controls on a graphical user interface. The user interface 38 may be integrated into the Navigation Host PC 168.

The neurosurgeon visualizes the MR images presented on the screen 36 of the Navigation Host PC 168 along with the coordinates of the robot tip, and navigates the robot tip in the desired direction entering commands 56 into the Navigation Host PC 168.

Accordingly, the commands 56 are transformed into corresponding control signals 54, which are applied to the robot (through the actuating mechanisms). Responsive to the control signals 54, the robot changes its position and/or configuration, and the Endoscout® sensors 140, 144 transform information corresponding to the changes in the position/configuration to the Endoscout® host PC 164, which, in turn, communicates with the Navigation Host PC 168. This process takes place whenever the robot body 20 is moved.

The images on the screen 36 may be updated in real-time for the neurosurgeon to analyze the situation and to further follow up with instructions/commands. In order to accomplish this, responsive to the new navigation instructions entered by the physician in the interface 38, the Navigation Host PC 168 generates new coordinates 172 (based on the neurosurgeon's commands to the robot) to the Scanner Host PC 160 which, in turn, obtains images corresponding to the new positions of the robot and displays them in real-time on the screen 36 thus providing the feedback routine.

The neurosurgeon may view images just in front of the tip of the robot, a coronal view centered around the midpoint of this image, and a sagittal view also centered around the center of this image. In this manner, the neurosurgeon is always able to see the intracranial operation site in front of the robot in all three orthogonal views.

The neurosurgeon may choose to terminate navigation, and obtain high-resolution diagnostic quality images which may further help in assessing the margins of the tumor and to make the decision to terminate or to continue further electrocauterization or other tissue liquefaction modality.

Referring to FIGS. 6A-6D, which are representative of a tracking and navigation routine in the subject system and returning to FIGS. 1 and 2, the tracking system (i.e., Endoscout® tracking system) receives the tracking point coordinates 59 from the Endoscout® sensor(s) positioned in the operative site 16 containing the target 18. The tracking point may be chosen manually based on the image from a camera attached to the MRI scanner 34.

Once the neurosurgeon enters a command 56 to move the tip of the robot closer to the target point (tumor) 18, the data transformation unit (data processor) 62 (residing, for example, in the Navigation Host PC 168) calculates one (or several) centers of rotation and actuates the corresponding actuating mechanism operatively coupled to the joint(s) corresponding to the center(s) of rotation to rotate respective links of the robot body 20 towards the target point 18.

Upon completion of the manipulation, the Endoscout® sensor 140 sends the new coordinates of the track point to the Endoscout® Host PC 164 which provides this information to the Navigation Host PC 168. In this way, the images on the Navigation Host PC 168 are updated in real-time for the neurosurgeon's use.

Figure 6A:
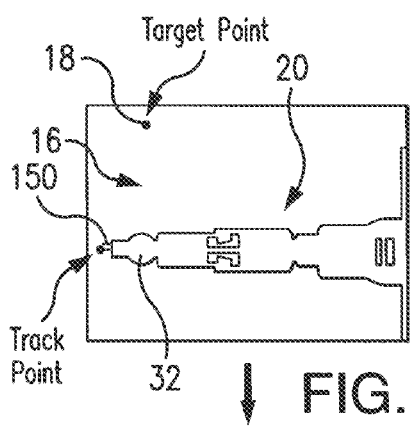
FIGS. 6A-6D illustrate the concept of the robot navigation relative to the target through real-time tracking and navigation in the present minimally invasive surgical robotic system.
Figure 6D:
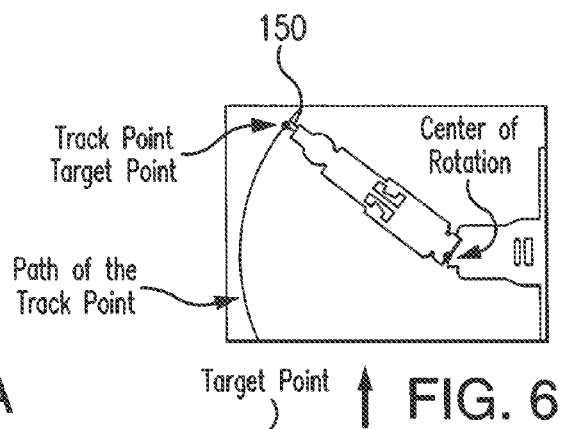
Figure 6B:
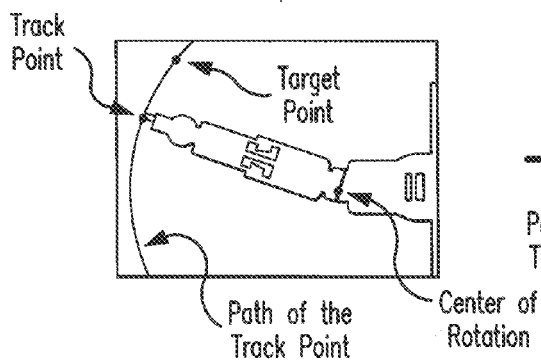
Figure 6C:
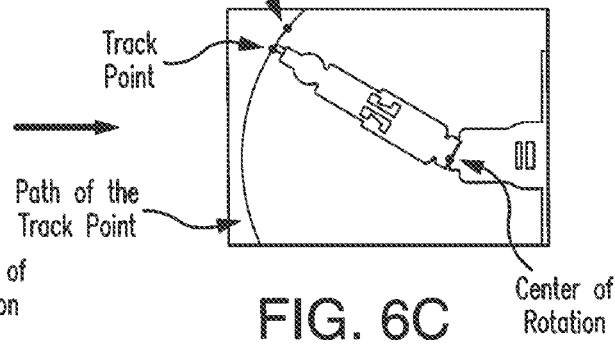

Since, as shown in FIG. 6B, the track point is still positioned far from the target point, the physician continues manipulation by entering further commands into the interface 38, i.e. Navigation Host PC 168. After obtaining the coordinates for the track point, the robot is moved further towards the target point under image guidance as shown in FIG. 6C, and this process continues until the track point is aligned with the target point as shown in FIG. 6D. At this point, the end-effector (track point) of the robot is at the tumor location, and the physician may issue a command to initiate a surgical procedure through the chosen modality by actuating the probes (end-effector) 150.

The motion of the robot is envisioned to be automatic from the initial configuration to the final configuration. The neurosurgeon does not have to enter the points continuously. If the initial and final positions are identified, then an autonomous motion planning strategy is used while providing real-time images to the neurosurgeon.

It is important to note that in addition to an automated system where the neurosurgeon teleoperatively directs the robot to assume a particular configuration and carry out the treatment for tissue biopsy or liquefaction, using one or another method, the subject system is provided with means enabling the physician to manually control the robot configuration by inputting a desired configuration of the robot on the screen by, for example, "clicking and dragging" the image of the end-effector presented on the virtual display while the system calculates the optimal manner to reach the desired robot configuration.

Referring again to FIGS. 1 and 5, two feedback control sub-systems are used in the present system, including image feedback control 58, and an actuator feedback control 64 which depends on the type of the actuator sub-system. The image feedback control 58 may sometimes fail, due to the noise in the images or due to missing the track point. Since safety is the most important factor for the surgical robot, a backup controller (feedback) 64 is implemented for the interventional device 12. The actuator feedback control unit 64 may be implemented as a temperature feedback control if the actuator sub-system 40 is built with SMA spring mechanism (as shown in FIG. 3). Feedback from sensing mechanisms within a given interventional devices 12 may communicate to the Navigation Host PC, the coordinates of which can be provided through the passive sensors.

Alternatively, if the actuator sub-system 40 is built with motors, as shown in FIG. 5, the actuator feedback control unit 64 may monitor position of the motors (acquired by appropriate sensors, such as for example, rotary encoders) corresponding to the configuration/position of the robot, and feed this information to the control sub-system 52 which may reside in the Navigation Host PC 168.

In the case of the SMA actuators (in addition to the navigation and high-resolution visualization), the Navigation Host PC 168 records temperature from appropriate sensors, such as, for example, thermocouples/RTD sensors. The data is made available on demand. The backup (actuator) control unit 64 monitors the temperature in each SMA spring and uses the temperature feedback as a backup control strategy. This is done primarily since there may be times when the imaging plane of the MRI may not align (due to delays in the repositioning of the operation site slices to be imaged) with the configuration of the robot. In those instances it is desired to enhance the images. For this purpose, the information from the SMA springs is used to determine the joint angle resulting in a required robot configuration.

While the image guided feedback control primarily runs in the foreground, the temperature data is collected from the thermocouples connected to the SMA springs in real-time and stored during robot operation. Alternatively, the back-up control unit 64 monitors the readings of the motors' rotary encoders (as shown in FIG. 5) which are stored during the robot operation and used on demand.

As shown in FIGS. 1 and 2, irrespective of the type of the actuators (hardware) used in the interventional device, the hardware feedback data 174 from the interventional device is monitored by the "Actuator Feedback" unit 64 (also referred to herein as a hardware feed-back unit). The hardware sensory feedback data 174 may be combined with image-based feedback 58 to have better tracking of the motion of the interventional device if one of the modalities does not provide the appropriate feedback signal to essentially control the motion of the interventional device. The redundant information (e.g., temperature feedback and image-feedback) may be helpful in enhancing the control capabilities of the subject system and potentially improve the safety of the surgical procedure.

In addition to the enhanced control of the robot motion, the hardware feedback 174 from the interventional device can be combined with the image-feedback 58 (acquired from MRI, for example) to provide input to the tracking and navigation system in terms of determining the coordinates of the next imaging slice.

Also, the combination of the hardware feedback data 174 coming from the interventional device with the PMFS (tracking information) 59 and the imaging data 50, for example, can be used for better tracking and navigation in the present system.

From the imaging prospective, and irrespective of the type of the interventional device, the feedback information 174 may be acquired from any sensory system reflecting the operation of the interventional device, including a reporter, a temperature measurement device placed in a proximity to the interventional device, as well as visual sensor(s). This will require the tracking technology to have some logic built into the tracking system and will be dependent on the type of the interventional device one is dealing with.

Combination of the robot's hardware sensory feedback data with either one (or both) of real-time images and tracking information, produces a combined control data which may be used by the Navigation sub-system to adjust the control signal applied to the interventional device in accordance with the combined data. In addition, the Navigation sub-system may use this feedback data in the subsequent image slice location computation, and in generating the optimal strategy for updating the subsequent slice imaging.

Referring again to FIG. 2, the raw data 50 from the imaging system 34 (for example, the MRI equipment) are exported from the Scanner Host PC 160 through the TCP/IP protocol and reconstructed within the Navigation Host PC 168. The MR images are displayed on the display 36 in real-time to aid surgical navigation. The Navigation Host PC 168 is able to switch from tracking mode to high resolution mode upon the neurosurgeon request, or such switching can be accomplished automatically. Both high resolution and tracking mode imaging techniques are used in this system. Switching from navigation mode to high resolution mode may occur through user interface 38 available on the Navigation Host PC 168.

A majority of the manipulations may be carried out to view the images in the tracking mode (which is in real-time mode of operation) to learn the position of the robot, or to obtain high-resolution images with desired contrast to assess whether to stop, change direction, or continue with the tissue liquefaction.

In one envisioned embodiment, the imaging manipulation may require the interface 38 to have a touch pad display or a joy stick to manipulate the direction in which the robot should move. The software on the Navigation Host PC 168 may be in a basic (or default) version, or may be flexible enough to accommodate the surgical practices of each neurosurgeon and their workflow. This may be provided through software modules incorporated into the base design of the user's interface.

Figure 7:
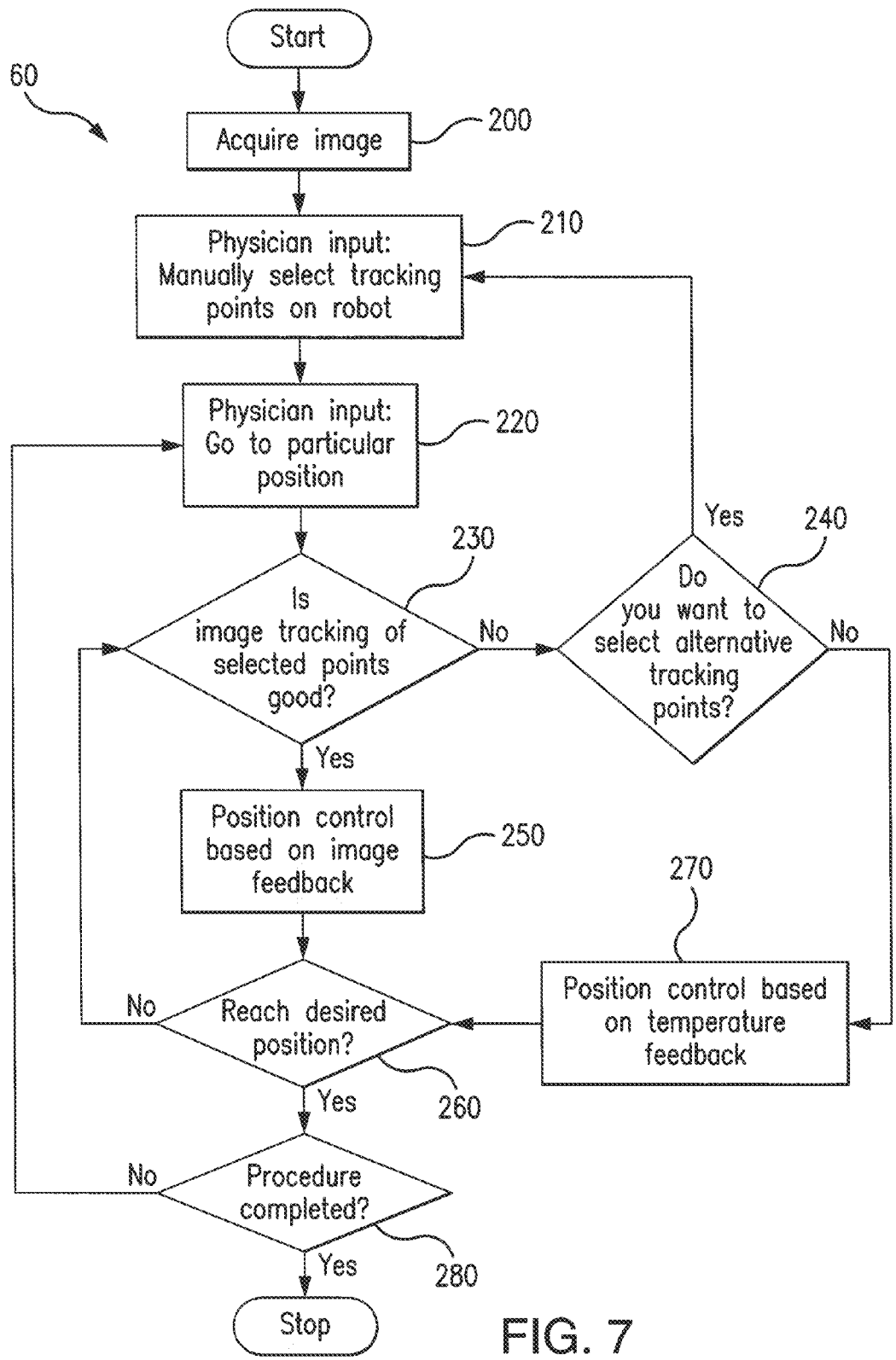
FIG. 7 is the flow chart diagram of the overall control process involving the system of the present invention.

Referring to FIG. 7, representing the flow chart of the overall process, i.e., the user-robot interaction software 60 (shown in FIG. 1), the procedure is initiated at step 200 where the MR image is acquired and presented on the Navigation Host PC 168.

The procedure is initiated with alignment of the robot joints so that the robot's configuration is straight at the start of the procedure. This position is registered in the MR image. It is envisioned that a calibration routine may be performed as part of the system operation. Further, in step 210, the neurosurgeon is prompted to enter commands, which may be entered by manually selecting tracking points on the robot. In further step 220, the physician is prompted to input the command "Go to Particular Position".

Upon receiving the command of the neurosurgeon entered in step 220, the logic requests in step 230 whether the image of the selected tracking points is satisfactory. If the answer is negative, the logic flows to step 240 and requests whether the neurosurgeon desires to select alternative tracking points. If the neurosurgeon agrees, the logic loops to step 210, where the neurosurgeon can select alternative tracking points on the robot. If however, in step 230, the image tracking of the selected points is satisfactory, the procedure follows to step 250 to control position based on the image feedback as was detailed in previous paragraphs.

If in step 240 the neurosurgeon does not desire to select alternative tracking points, the procedure follows to block 270 and the control sub-system controls the position based on the temperature (or, alternatively, on motors rotary encoders' readings) feedback. At this point, the temperature data collected in real-time and stored during the robot operation, are used to determine the joint angle based on the collected temperature data.

From step 250, and/or alternatively from step 270, the process flows to logic block 260 where the system requests the neurosurgeon to determine whether the desired position has been reached. If the desired position has been reached, the logic flows to block 280 where the neurosurgeon is requested as to whether the procedure is completed. If the procedure is completed the process is terminated.

If however in step 260, the desired position has not been reached, the logic loops to the step 230 and prompts the neurosurgeon to answer whether the image tracking of the previously selected points is satisfactory.

In step 280, if the procedure is not completed, the logic returns to step 220, and prompts the neurosurgeon to input another particular position of interest.

The materials used for the robot sub-system parts are selected from the standpoint of minimal image distortion and corresponding high SNR (signal-to-noise ratio), which, in turn, may help with better localization of the robot body as well as the localization of the end-effector with respect to the tumor. In addition to plastics, MRI compatible metals may be used for the body of the robot, such as brass, titanium, etc. The robot body is enveloped into a medically inert plastic material 170 (shown in FIG. 3) which smoothes the overall configuration of the robot to prevent direct contact between the moving parts of the robot and patient tissue in the intraoperative site in order to reduce trauma to the brain while the robot is being navigated.

The present system is adaptable to a number of imaging techniques. As an example, the system described herein, is specifically suited for MRI pulse sequences to enable communication with the robot for real-time imaging manipulations. The pulse sequences used are envisioned, for example, as standard rapid imaging sequences, which are commonly provided by manufacturers of the MR equipment.

In the real-time tracking sub-system 61, the Endoscout® sensor includes a set of three passive orthogonal coil sensors with a total dimension of 5 mm in length and 1.5 mm diameter. This sensor picks up the changing gradient fields (MRI gradient pulses) in the magnet of the MRI scanner during the imaging process. This design represents a PMFS (Passive Magnetic Field Sensor) system, called the Endoscout® (Robin Medical Inc., Baltimore, USA), which uses specialized gradient pulses that are embedded within an imaging pulse sequence to induce currents in a sensor assembly containing three orthogonal sets of coils.

System calibration may be performed once per scanner using a grid of sensors that spans the entire diameter and length of the bore of the magnet. During calibration, the sequence with the embedded tracking gradients is run and the currents in the sensors are digitized, for creating a map of the field space, which may be used to determine the location and orientation of the sensors.

During the normal tracking operation using a single sensor and running the special gradient sequence, the Endoscout® system digitizes the currents induced across the sensor's coils at a rate of 200 kHz or higher. The induced currents are then compared by an optimization algorithm to the values in the previously stored map of the field space to determine the position and orientation of the sensor.

The prototype system was built which included a slave and master robot. The slave robot is represented by the interventional robotic device 12 positioned within the MRI scanner. The PMFS was mounted on the "head" of the robot 12, and was used to provide the real-time position and orientation of the end-effector assembly within the magnet. The master robot, i.e., the Navigation sub-system and the Robot Host PC, was located in the MRI control room, and allowed the operator (surgeon) to control the position and orientation of the slave robot 12, as well as receive haptic feedback from the force sensors as the end-effector (for example, a biopsy needle, was inserted or withdrawn).

Depending on the type of the imaging sequence used during the tracking mode or 'spot imaging' mode, specialized gradient pulses are embedded into the imaging pulse sequence, and the voltage from these pulses is captured by the passive coil sensors and is digitized at a rate of 40 kHz or higher to be subsequently analyzed to determine the location and the orientation of the sensor, as presented in J. Hong, et al., "Real-time magnetic resonance imaging driven by electromagnetic locator for interventional procedures and endoscopic therapy" in Surgical endoscopy, 2008. 22(2): p. 552-6; Y. Kukrumi, et al., "MR-guided microwave ablation for malignancies. International journal of clinical oncology/Japan Society of Clinical Oncology, 2007. 12(2): p. 85-93, and A. M. Tang, et al., "Simultaneous ultrasound and MRI system for breast biopsy: compatibility assessment and demonstration in a dual modality phantom," IEEE Transactions on Medical Imaging, 2008, 27(2): p. 247-54.

The location and orientation is calculated in the Endoscout® Host PC 164 or in the Navigation Host PC 168 by comparing the voltages from the real-time data acquired by the sensor(s) in the Tracking sub-systems 61 to pre-calibrated maps 176 of the gradient magnetic fields and can be exported in the form of coordinates 166 from the Endoscout® Host PC system 164 in real-time and used to navigate by the Navigation Host PC 168 from one slice scan location to another to track the end-effector (for example, the tip of the needle) by communicating the Scan Plane Update 172 to the Scanner Host PC 160.

The suitability of the Endoscout® for real-time imaging was tested using an in-house developed 2-D motion platform that was built with a moving platform over which a circular disc attached to the Endoscout® sensor was placed. Driven by a DC motor, the platform was moved in the z-direction (translation) by about 5 inches with a quarter turn as it traversed this distance.

Figure 8A:
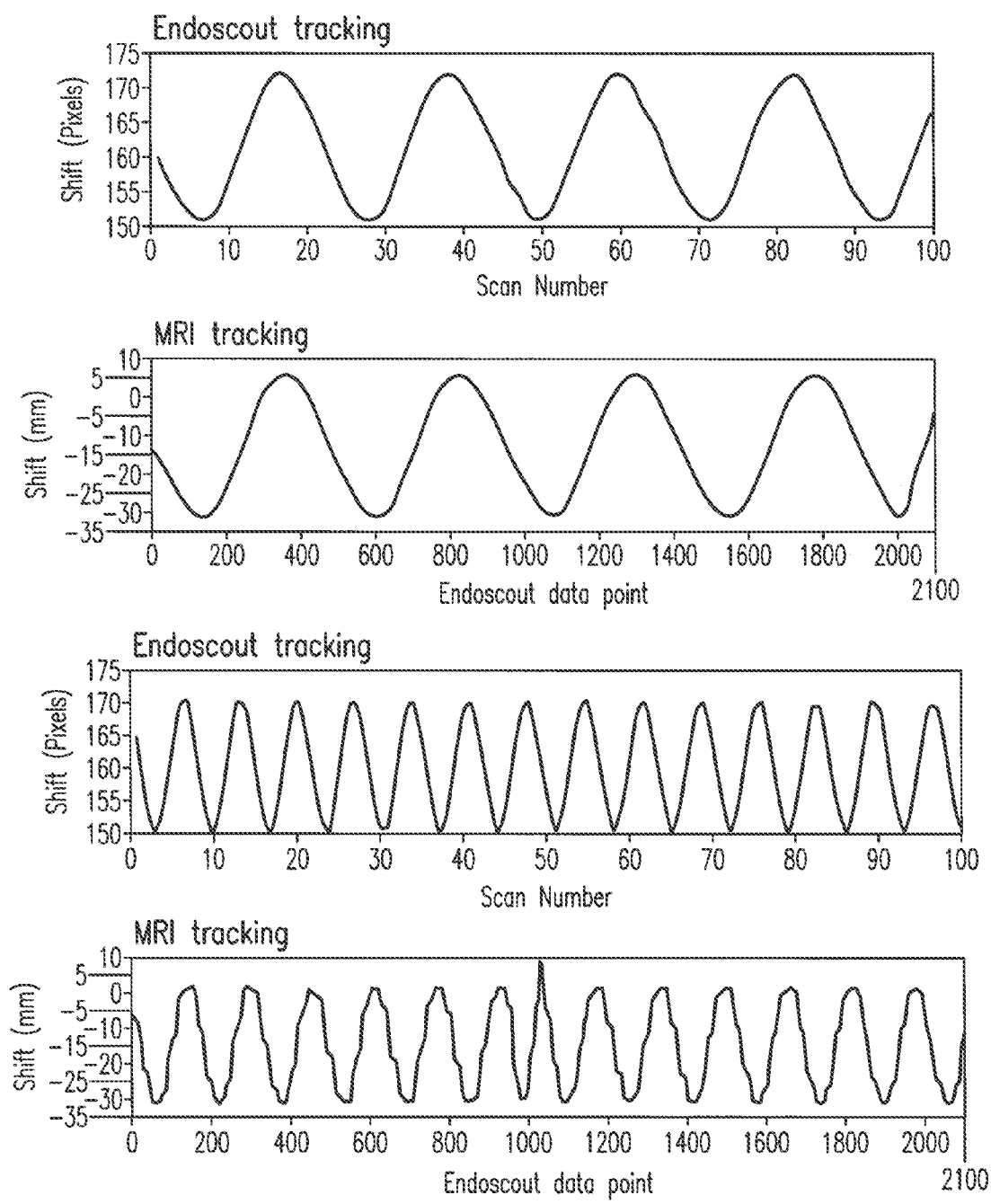
FIG. 8A represents diagrams corresponding to cyclical motion of the phantom as measured by the coordinates determined by the Endoscout® and the coordinates reported by the MRI system at two different velocities.
Figure 8B:
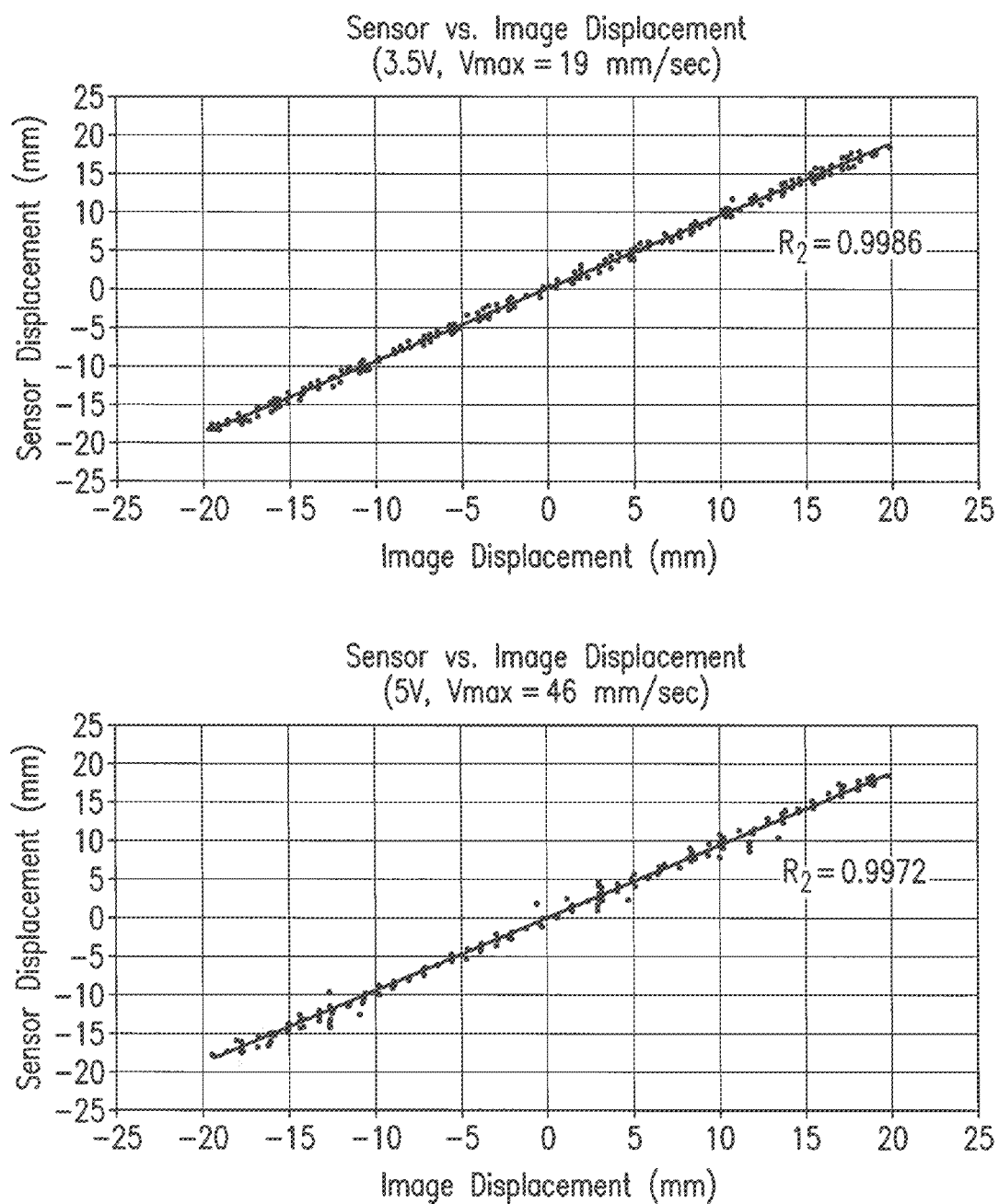
FIG. 8B represent diagrams correlating coordinates produced by Endoscout® and reported by MRI at two different velocities.

To check the ability to track the Endoscout® sensor, slice offset coordinates were provided in real-time to the Scanner Host PC 160 which in turn were computed from the coordinates provided by the Endoscout® host PC 164. This allowed independent comparison of the physical coordinates of the Endoscout® sensor and the coordinates obtained from the MR images. As evidenced from FIGS. 8A-8B, there was a satisfactory concordance between the location of the phantom determined by the Endoscout® sensor and that determined by the MR scanner at different motion velocities. FIG. 8A is representative of the cyclical motion of the phantom as measured by the coordinates determined by the Endoscout®, and the coordinates reported by the MRI system at two different velocities. Good concordance between the two independent measures is seen demonstrating that real-time tracking can be performed using Endoscout® with great accuracy. FIG. 8B shows a high correlation between Endoscout® and MR coordinates at two different velocities. There is a minimal increase in the tracking error at higher velocities, with the error being less than ±1 mm.

The ability to track in real-time and use this information to update the slice position is important to the success of any image guided interventional procedure as it provides a clear view of the tissues in three orthogonal planes in and around the tip of the robot device that the surgeon uses and guides towards the target.

Figure 9A:
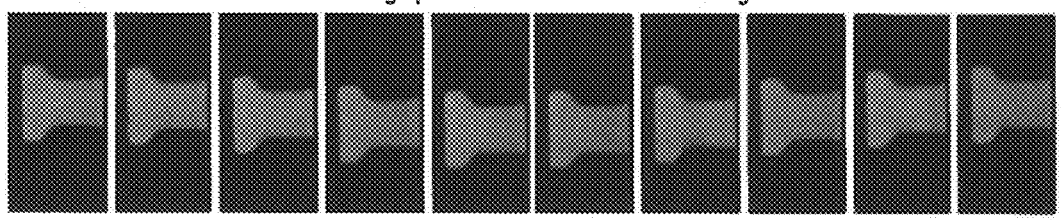
FIGS. 9A-9B represent sets of images corresponding to the motion of an object without tracking information (FIG. 9A) and with the tracking information acquired from the Endoscout® (FIG. 9B)
Figure 9B:
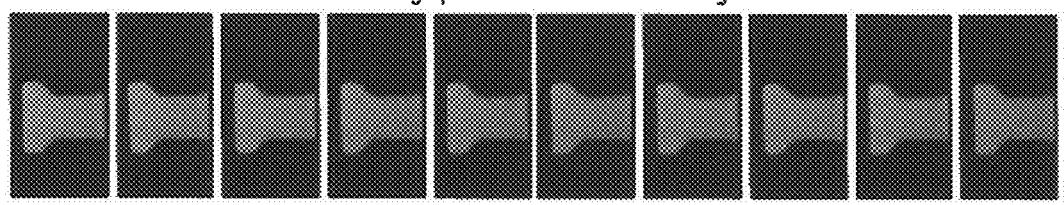

FIGS. 9A and 9B demonstrate the tracking capability where the top row (FIG. 9A) of images shows the normal motion of the phantom along the z-direction when the tracking information from the Endoscout® sensor was not used.

The bottom row of images (FIG. 9B) was obtained using the tracking information from the Endoscout® sensor to compute the coordinates for the next scan slice location based on the sensor location to be able to precisely follow the sensor by communicating with the Scanner Host PC 160 which continuously updates the scan slice location based on the sensor location. Hence the phantom (image) appears to be stationary although it has a movement of 5 mm on average between each frame (scan slice) in the z-direction.

Such tracking concepts provides the necessary visualization to allow the surgeon to see the tissue that the specific device will be interacting with, and at the same time obtain high-resolution images on demand for detailed surgical planning.

The choice of the Endoscout® is based on the small size of the sensor, and the fact that it can be easily attached at the tip of the interventional device, as well as the 6-DOF tracking ability with small error provided by the three orthogonal coils of the Endoscout® sensor. Further improvements in accuracy may be promoted by the use of an additional Endoscout® sensor positioned at a spot along the length of the interventional robot device.

The Endoscout® sensor can use high-resistance wires that do not heat as much as a copper wire during scanning, and thus is free of heating hazard.

The Endoscout® sensor is small, sterilizable, biocompatible, determines the location and orientation with six degrees of freedom, and has no restriction such as requiring line-of-sight to a reference piece of equipment, and thus provides an unique solution for significant advancement in image guided interventions.

As shown in FIG. 2, an image acquisition sub-system 300 is provided in operative coupling to the Navigation Host PC 176 to perform images reconstruction. A real-time undersampled projection reconstruction was implemented using golden ratio projection ordering as described in K. M. Koch, et al., "Magnetic resonance imaging near metal implants", Journal of magnetic resonance imaging": JMRI, 2010. 32(4): p. 773-87, and Schaeffter T., et al., "Simultaneous imaging and R2* mapping using a radial multi-gradient-echo (rMGE) sequence", J. Magn Reson Imaging, 2006. 24(4): p. 939-944.

Projection imaging in general allows flexible reconstruction of images for a given spatial and temporal resolution while allowing shorter echo times and reducing susceptibility artifacts as presented in S. Winkelmann, et al., "An optimal radial profile order based on the Golden Ratio for time-resolved MRI", IEEE Transactions on Medical Imaging, 2007. 26(1): p. 68-76.

Trade-off between temporal and spatial resolution can be made with the use of projection imaging with flexible ordering schemes and the ability to freely reconstruct images with any number of projections depending on the temporal and spatial resolution requirements.

Specifically, the golden ratio projection ordering scheme permits dynamic tradeoffs to be made between spatial and temporal resolution as seen in FIGS. 10A-10E within a single dataset. When the number of projections equals a Fibonacci number, the reconstruction error compared to uniformly-sampled projection acquisition is minimal, allowing images to be reconstructed at a higher temporal resolution, but with lower spatial resolution. Incorporation of parallel imaging with projection imaging further reduces scan time with increased spatial and temporal resolution as seen from comparison between the images shown in FIGS. 10A-10B. The image shown in FIG. 10D was obtained 8-times faster compared to the image shown in FIG. 10C and compares favorably to fully sampled reference image shown in FIG. 10E.

However, this low resolution image is likely sufficient to identify the location of the interventional device. Tracking information from low resolution images (high temporal resolution) can than be used to obtain orthogonal high-resolution images 'on demand' by increasing the number of projections (increased scan time) from the same pulse sequence to obtain high resolution images in any plane at the location of the device tip for planning and guidance. This scheme is advantageous in that it allows flexible image reconstruction when imaging coils not optimized for parallel imaging techniques are required for access to the patient.

A real-time 2D multi-slice gradient echo pulse sequence was developed on a 3T MR scanner (Tim Trio, Siemens Medical Solutions, Malvern, Pa.). Real-time control was performed via TCP/IP connection from the reconstruction computer 300 to a server connected to the Ethernet network of the MR scanner. The position server was a multi-threaded Java program which allows interactive control of the slice position and orientation from a GUI and/or other networked entities via TCP/IP.

To enable real-time tracking of position within the MR scanner, the FDA-approved PMFS (Endoscout, Robin Medical Inc., Baltimore, Md.) was used. A 2D gradient echo pulse sequence was modified to include bi-polar tracking gradients to measure absolute position and orientation of the PMFS.

To test the position and orientation accuracy of the PMFS, a motion simulator was constructed to provide in-plane sinusoidal translation and rotation. Image-based registration was performed to estimate motion parameters obtained from the image data and compared to the output of the PMFS.

To test the capability of the PMFS to enable real-time tracking and dynamic slice positioning, the position output of the Endoscout® was continuously fed into the position server via TCP/IP, and the motion simulator was operated to provide translational motion.

Accuracy of the PMFS for tracking was compared to inter-frame image-based registration of the moving phantom and was found to be to be highly linear ($R2>0.98$) and accurate (position error=0.83 mm±0.70 mm; rotation error=1.80°±1.35°).

Accurate and dynamic tracking was attainable using the PMFS. While image motion is greatly stabilized during dynamic tracking, some residual motion remains, likely due to intraframe motion. Higher frame rate imaging and methods that model object motion (e.g., velocity) may be used to improve the dynamic slice positioning.

Several aspects are contemplated in the present system with respect to pulse sequence optimization:

(1) optimization of the pulse shapes for accurate targeting of Endoscout® under various conditions;

(2) improving the frame rate of image acquisition; and (3) optimization of pulse sequences for tracking.

Figure 11:
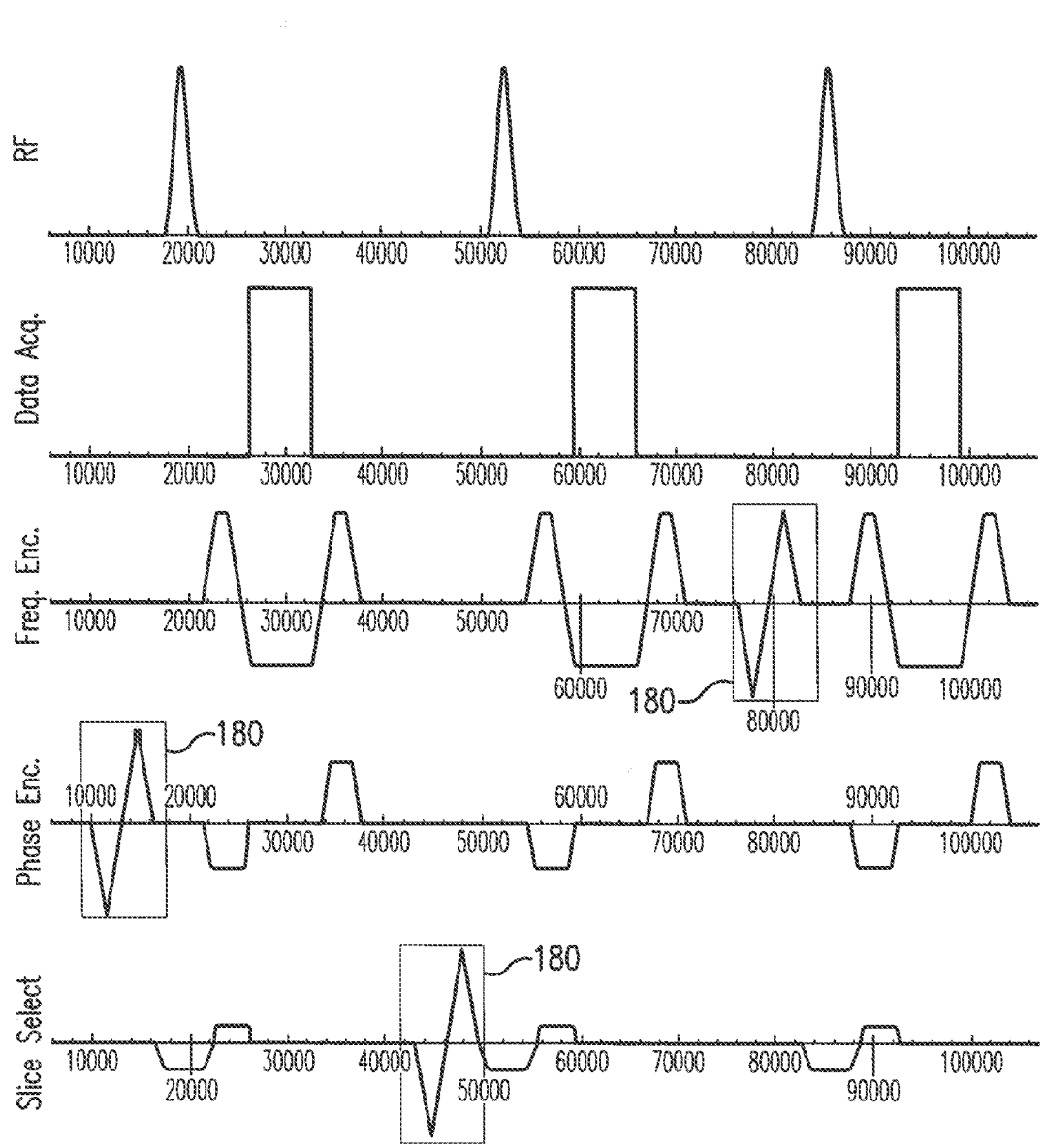
FIG. 11 represents pulse sequence diagrams for True FISP acquisition used in the present system.

The accuracy of the Endoscout® for the targeting functionality is a function of the duration and strength of the bipolar pulses 180 used in each of the orthogonal gradient profiles of a given pulse sequence as shown in FIG. 11. A pulse sequence suite specific to the Endoscout® is developed that have the calibrated bipolar pulses 180 incorporated to provide an accuracy of less than 1 mm over the brain imaging field of view of about 25 cm.

In experiments, the sampling rate used in the Endoscout® was 400 kHz or higher which is faster than the time required to obtain a single projection. The additional information from the Endoscout® from each projection was continuously used to predict the location of the Endoscout® to prescribe the next projection by the Navigation Host PC 168 which in turn generated the coordinates necessary for the next slice position to obtain images of the robot tracked during motion.

For optimizing pulse sequences, the real-time undersampled projection reconstruction was explored using golden ratio projections. Projection acquisitions allow visualization of small fields of view (including rectangular) with no wrap-around, as presented in P. E. Larson, et al., "Anisotropic field-of-view shapes for improved Propeller imaging". Magnetic resonance imaging, 2009. 27(4): p. 470-9; and P. Z. Larson, et al., "Anisotrophic field-of-views in radial imaging", IEEE Transactions on Medical Imaging, 2008. 27(1): p. 47-57.

To improve temporal resolution, a reconstruction method was developed for multiple-coil under-sampled projection acquisition data where the angular sub-sampling can be reflected as one-dimensional aliasing in a transform domain. This new method allows the advantageous combination of under-sampled projection imaging and parallel imaging to greatly accelerate imaging, which can be implemented in a direct non-iterative manner suitable for real-time imaging (C. O. Schirra, et al., "Accelerated 3D catheter visualization from triplanar MR projection images", Magnetic resonance in medicine: official journal of the Society of Magnetic Resonance in Medicine/Society of Magnetic Resonance in Medicine, 210. 64(1): p. 167-76).

The goal of the routine was to obtain temporal resolution of less than 100 ms for a single slice. With just 16 projections and 12 independent receiver channels as shown in FIG. 10A-10E, the present method can provide acceleration rates of 16 with similar resolution compared to standard Cartesian methods. This translates to improved frame rates suitable for tracking the interventional device at multiple frame rates using standard sequences such as gradient echo and True-FISP.

The current implementation of the communication between the Scanner Host PC 160, Endoscout® Host PC 164 and the interventional device's (biopsy needle, RF-ablator, microbot, etc.), i.e., Robot Host PC 162 is outlined in FIG. 2.

In operation, the robot is guided by the interventionalist (surgeon, user) 57. The location of the robot is continuously tracked by the Endoscout® sensor(s) which in turn provides the location information 166 of the robot's end-effector to the Navigation Host PC 168. The Navigation Host PC 168 in turn uses the location information 166 to predict the next slice location based on its trajectory history which it communicates with the Scanner Host PC 160.

In an alternative implementation, it is contemplated that network delays are further minimized by incorporating the logic available in the Endoscout® Host PC 164 and the specific host PC of the device (if necessary) into the Navigation Host PC 168. The calibration file 176 may be provided in the Navigation Host PC 168 (as an alternative to residing in the Endoscout® Host PC 164) to transform the Endoscout® coordinates 166 to the MRI scanner coordinates 172.

Device tracking information 59 (and/or 166) can be used for future slice prescription in real-time. Flexibility for operating in the tracking mode or in the high-resolution mode is provided to the Navigator Host PC interface by appropriately adjusting the number of projections needed for a given image. A single unified user interface on the independent Navigation Host PC 168 is developed that integrates information from both the Scanner Host PC 160 and the Endoscout® interface 164 to enable communication with the scanner 34, performing off-line reconstruction all within the confines of a Graphical User Interface (GUI) 182 that will allow for easy visualization during tracking, analyzing high resolution images, and provide assistance in planning further intervention.

Various methods for projection ordering may be explored for optimal reconstructions with as few projections as possible and continual update of images using various projections with special consideration for off-resonance effects especially associated with True-FISP (Fast Imaging with Steady State Precession) techniques. It is contemplated that compressed sense techniques may be used for further improvement in temporal resolution. (R. Otazo, et al., "Combination of compressed sensing and parallel imaging for highly accelerated first-pass cardiac perfusion", MRI. Magnetic resonance in medicine: official journal of the Society of Magnetic Resonance in Medicine/Society of Magnetic Resonance in Medicine, 2010. 64(3): p. 767-76).

Direct capture of the raw data from projection imaging may also be used in the present system which will be reconstructed and displayed within the GUI 182 of the Navigation Host PC 168.

The GUI 182 of the Navigation Host PC 168 may be an integrated real-time system that will help the clinician to navigate the interventional device, for example, to optimally resect a lesion through real-time visualization of the operation field. The Navigation Host PC 168 is a convenient and advantageous as together with the interventional robot device, it may be easily integrated into any existing MRI scanner on the market.

While the standard scanner interface may be used to initiate the surgical procedure, the Navigation Host PC 168 is contemplated with all the logic necessary for targeting, navigating, and visualizing changes to tissue during intervention through the use of the GUI 182.

The Scanner Host PC 160 and the Navigation Host PC 168 may be networked via a standard Ethernet connection and to allow bidirectional communication to transfer image and/or raw data information from the Scanner Host PC 160 to the Navigation Host computer 168. The Ethernet connection within the local network of the MRI scanner allows a data transfer rate of up to 125 MB/s, which would allow transfer of up to 1,000 16-bit images/s with 256×256 and should be sufficient for the surgical application of the system.

Other options that provide for faster processing and acquisition include the use of the spiral imaging.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of the elements may be reversed or interposed, all without departing from the spirit or scope of the invention as defined in the appended claims.

What is being claimed is:

1. A system for telemetrical control of an interventional device for minimally invasive surgical procedure, comprising:
   a Magnetic Resonance Imaging (MRI) scanner sub-system operated to produce substantially in real-time MR images of an operative site comprising a target of interest;
   an interventional device disposed at said operative site within said MRI scanner sub-system;
   a tracking sub-system operatively coupled to said MRI scanner sub-system and operating concurrently therewith, wherein said tracking sub-system is configured to automatically and continually produce tracking information corresponding to a location of said interventional device within said operative site, said tracking information being produced based on gradient fields of said MRI scanner sub-system;
   a processor controlled navigation sub-system operatively coupled to said tracking sub-system, said MRI scanner sub-system, and said interventional device, wherein said navigation sub-system is configured to:
   (a) integrate said tracking information with said real-time MR images, (b) display said substantially real-time MR images of said operative site generated by said imaging MRI scanner sub-system, and (c) fluidly interface with a user to present, in a continuous fashion, said real-time MRI images and said tracking information, and to receive the user's commands to telemetrically control said interventional device to reach said target of interest in an optimal manner for an intended interaction therewith based on at least said substantially in real-time MR images and said tracking information.

2. The system of claim 1, further comprising a processor controlled control sub-system operatively coupled to said navigation sub-system and said interventional device, wherein said control sub-system is configured to generate control signals responsive to the user's commands input into said navigation sub-system and to apply said control signals to said interventional device to control the motion thereof in said operative site relative to said target of interest.

3. The system of claim 2, wherein said tracking sub-system further includes a sensor sub-system integrated with said interventional device, wherein said sensor sub-system includes at least one passive magnet field sensor (PMFS) positioned in proximity to a tip of said interventional device.

4. The system of claim 3, wherein said sensor sub-system further includes at least one second PMFS positioned at a predetermined location along the length of said interventional device.

5. The system of claim 3, wherein said imaging MRI scanner sub-system further generates images based on an imaging pulse sequences, wherein said tracking sub-system uses predetermined tracking gradient pulses embedded in said imaging pulse sequences to induce currents in said sensor sub-assembly, and wherein said induced currents are processed to determine the position and orientation of said at least one PMFS.

6. The system of claim 5, further comprising pre-calibrated maps of induced currents in correspondence to said at least one PMFS location within said MRI scanner sub-system, wherein said navigation sub-system is configured to correlate said induced currents from said at least one PMFS to a corresponding location in said pre-calibrated maps.

7. The system of claim 5, wherein said navigation sub-system is further configured to process, in real-time, coordinates of said at least one PMFS, to compute coordinates of a subsequent imaging slice based on said at least one PMFS coordinates, and to update, in real-time, said subsequent slice location during said surgical procedure.

8. The system of claim 1, further comprising an image acquisition sub-system operatively coupled to said navigational system to perform reconstruction of said images.

9. The system of claim 8, wherein said image acquisition sub-system is based on a real-time under-sampled projection reconstruction routine using golden ratio projection ordering and specific undersampling routines.

10. The system of claim 7, wherein said navigation sub-system communicates said coordinates of said subsequent imaging slice to said MRI scanner sub-system substantially in real-time for the subsequent image taking.

11. The system of claim 9, wherein said system is configured to operate in a tracking imaging mode and in a high resolution spot imaging mode, and wherein said navigation sub-system is further configured to adjust the number of projections needed for operating in the high-resolution or the tracking modes of operation with various contrast.

12. The system of claim 1, wherein said navigation sub-system comprises a user interface including a display sub-system.

13. The system of claim 1, wherein said interventional device includes a minimally invasive robotic sub-system compatible with said MRI scanner sub-system, wherein said robotic sub-system includes at least one end-effector adapted for said intended interaction with said target of interest, and wherein said user's commands include activation of said end-effector once said interventional device reaches said target of interest, and wherein said at least end-effector is adapted for tissue biopsy or tissue liquefaction of said target of interest.

14. A method for telemetrically controlling an interventional device during a minimally invasive surgical procedure, comprising the steps of:

positioning an operative site containing a target of interest into a Magnetic Resonance Imaging (MRI) scanner sub-system;

introducing an interventional device adapted for a surgical procedure to said operative site containing said target of interest;

integrating a tracking sub-system with said interventional device, and actuating said tracking sub-system to automatically and continually generate, substantially concurrently with said MRI scanner operation, tracking information corresponding to a location of at least a portion of said interventional device within said operative site;

operatively coupling a navigation sub-system to said tracking sub-system, said interventional device, and said imaging MRI scanner sub-system; and configuring said navigation sub-system to operate through the steps of:

displaying, substantially in real-time, MR images acquired from said MRI scanner sub-system, integrating said substantially real-time MR images with said tracking information obtained automatically and continually by said tracking sub-system based on gradient fields of said MRI scanner sub-system, and generating coordinates of said tracking sub-system in said operative site, and upon receipt of a command from a user to control the interventional device, issuing a control signal applied to said interventional device to actuate a required motion thereof relative to the target of interest for an intended surgical interaction therewith.

15. The method of claim 14, wherein said MRI scanner sub-system generates said MR images in correspondence with predetermined imaging pulses sequences, further comprising the steps of:

embedding pre-determined tracking gradient pulses in said imaging pulses sequences, inducing currents in said tracking sub-system by said tracking gradient pulses, and processing said induced currents to determine a real-time position of said tracking sub-system.

16. The method of claim 15, further comprising the steps of:

computing, in said navigation sub-system, substantially real-time coordinates of said tracking sub-system, computing, in said navigation sub-system, substantially real-time coordinates of a subsequent image slice based on said coordinates of said tracking sub-system, dynamically updating, substantially in real-time, said subsequent image slice location during the surgical procedure, and actuating said imaging sub-systems accordingly for taking said subsequent image slice.

17. The method of claim 15, further comprising the steps of:
operatively coupling an image-acquisition sub-system to said navigation sub-system,
performing images reconfiguration using golden ratio projection ordering, and
adjusting the number of projections needed for a high resolution imaging mode or tracking imaging mode of operation.

18. The method of claim 17, further comprising the steps of:
optimizing the imaging pulse sequences by:
embedding said tracking gradient pulses in the format of calibrated bipolar pulses having a predetermined duration and strength, and
using a frame rate of image acquisition exceeding the time duration requirement for obtaining a single projection.

19. The method of claim 16, further include the steps of:
monitoring feedback data corresponding to said interventional device position,
combining said feedback data with at least one of said substantially real-time images and said tracking information data, thereby obtaining combined data,
adjusting said control signal applied to said interventional device in correspondence to said combined data, and
communicating said feedback data to said navigation sub-system to compute, based on said combined data, said subsequent image slice location, and generate an optimal strategy for updating the subsequent slice imaging.

* * * * *